United States Patent [19]
Cavalieri et al.

[11] Patent Number: 5,849,906
[45] Date of Patent: Dec. 15, 1998

[54] ANTIGENIC CONJUGATES OF POLYCYCLIC AROMATIC HYDROCARBONS TO NUCLEOSIDES

[76] Inventors: Ercole Cavalieri, 22635 Wilson Ave., Waterloo, Nebr. 68069; Eleanor Rogan, 8210 Bowie Dr., Omaha, Nebr. 68144

[21] Appl. No.: 636,856

[22] Filed: Apr. 23, 1996

Related U.S. Application Data

[63] Continuation-in-part of Ser. No. 300,106, Sep. 2, 1994, abandoned.

[51] Int. Cl.[6] .......................... C07H 1/00; C07H 19/073; C07H 19/173
[52] U.S. Cl. .......................................... 536/55.3; 536/22.1
[58] Field of Search .................................. 536/55.3, 22.1

[56] References Cited

U.S. PATENT DOCUMENTS

| | | | |
|---|---|---|---|
| 4,016,043 | 4/1977 | Schuurs et al. | 195/103.5 |
| 4,018,653 | 4/1977 | Mennen | 195/127 |
| 4,196,265 | 4/1980 | Koprowski et al. | 435/2 |
| 4,271,145 | 6/1981 | Wands et al. | 424/85 |
| 4,424,279 | 1/1984 | Bohn et al. | 436/534 |

OTHER PUBLICATIONS

Rogan et al. J. Amer. Chem. Soc. 110:4023–4029, 1988.
G. Kohler et al., (1976) Eur. J. Immol 6: 511–519.
G. Kohler et al., (1975) Nature 256: 495–497.
C. Reading (1983) J. Immunol. Meth. 53: 261–291.
Wilk and Girke, Journal of the National Cancer Institute, 49: 1585–1597 (1972).

*Primary Examiner*—Gary L. Kunz
*Attorney, Agent, or Firm*—Dann, Dorfman, Herrell and Skillman

[57] ABSTRACT

The present invention relates to novel immunologic reagents and their use in assays for the detection of polycyclic aromatic hydrocarbon (PAH)-DNA or heteropolycyclic aromatic hydrocarbon (HAH)-DNA adducts. These adducts are uniquely important biomarkers for cancer risk due to exposure to environmental PAH and HAH pollutants. More particularly, this invention relates to new hapten-protein conjugates and their use as antigens in the production of antibodies for use in immunological assays for PAH and HAH biomarkers. The invention also relates to novel, chemically-pure DNA adducts of PAH or HAH which form the haptenic moieties of the conjugates of this invention, and to improved methods for their synthesis and isolation.

15 Claims, 8 Drawing Sheets

ANTIGENIC CONJUGATES OF POLYCYCLIC AROMATIC HYDROCARBONS TO NUCLEOSIDES

This application is a continuation-in-part of U.S. application, Ser. No. 08/300,106, filed Sep. 2, 1994, now abandoned. Pursuant to 35 U.S.C. Section 202(c), it is hereby acknowledged the the United States government has certain rights in the invention described herein, which was made in part with funds from the National Institutes of Health.

FIELD OF THE INVENTION

The present invention relates to novel immunologic reagents and their use in assays for the detection of polycyclic aromatic hydrocarbon (PAH)-DNA adducts as well as heteropolycyclic aromatic hydrocarbon (HAH)-DNA adducts. These adducts are uniquely important biomarkers for cancer risk due to exposure to environmental PAH and HAH pollutants. More particularly, this invention relates to new hapten-protein conjugates and their use as antigens in the production of antibodies for use in immunological assays for PAH and HAH biomarkers. The invention also relates to novel, chemically-pure DNA adducts of PAH or HAH which form the haptenic moieties of the conjugates of this invention, and to improved methods for their synthesis and isolation.

BACKGROUND OF THE INVENTION

PAH and HAH are not natural compounds that exist in the environment, rather, they are created by the incomplete combustion of organic substances. Metabolites of these carcinogenic organic compounds can react with DNA to form covalently bound adducts. Adducted DNA bases, spontaneously released from the DNA, represent a major expression of PAH or HAH-induced genetic damage, a precursor to PAH or HAH-induced cancer. These "depurination" or "depyrimidination" adducts are present in biological fluids (including urine), and are direct indicators of PAH or HAH-induced DNA damage and risk for cancer. Such adducts are considered to be essential intermediates in the mechanism of chemical carcinogenesis. The reliable detection and quantitation of such adducts in biological fluids, using well-defined PAH or HAH standards provides a powerful approach to determining the risks associated with exposures to carcinogens which may be present as environmental pollutants. Detection and quantitation of such depurination or depyrimidination adducts can be by a variety of immunoassay methods ranging, for example, from sophisticated enzyme-linked immunosorbent assays (EIA) to elegant and simple radial immunodiffusion (RID) assays.

An immunoassay for the identification of biologically-formed PAH-DNA or HAH-DNA adducts requires preparation of synthetic authentic adducts. Since these adducts are too small to be capable of producing antibodies, each must be linked to an immunogenic protein and the resultant antigenic conjugate used to produce specific antibodies for use in immunoassays for the native adducts present in biological fluids.

It is an object of this invention to provide methods for preparing synthetic, authentic DNA-PAH or DNA-HAH adducts. These adducts when linked to an immunogenic protein carrier comprise the haptenic portion of the resulting conjugate. It is also an object of this invention to provide immunogenic conjugates of such adducts. A further object is to provide specific antibodies and capture agents for use in immunoassays for naturally occurring DNA-PAH or DNA-HAH adducts. These and other objects of this invention are described more fully hereinafter.

DESCRIPTION OF THE INVENTION

In accordance with one embodiment of this invention there are provided synthetic adducts of polycyclic aromatic hydrocarbons (PAH) or heterocyclic polycylic aromatic hydrocarbons (HAH) and a purine base, i.e., adenine (A) or guanine (G) or a pyrimidine base, i.e., cytosine (C), thymidine (T) or uracil (U). These adducts when conjugated to an immunogenic protein as discussed hereinafter, form the haptenic portion of the novel conjugates of this invention.

The PAH or HAH can be any PAH or HAH found in the environment. These compounds are well known and have been described in the literature. (For example see G. Grimmer, "Relevance of polycyclic aromatic hydrocarbons as environmental carcinogens", in Polycyclic Aromatic Compounds: Synthesis, Properties, Analytical Measurements, Occurrence and Biological Effects; P. Garrigues and M. Lamotte, eds. Gordon and Breach, Langhorne, Pa., 1993, pp. 31–41) Generally, these compounds have been artificially introduced into the environment as a result of incomplete combustion of organic substances. They are found in tobacco smoke, of both primary and secondary type, and in other atmospheric pollutants, for example, from industrial sources, in particular, petroleum refineries, chemical manufacturing facilities, steel manufacturing facilities, electrical generating plants fueled by fossil fuels, and the like. Although the compositions of these environmental PAH and HAH can vary widely, the marker compounds of interest for the purposes of this invention can be delimited by the fact that they must be capable of adduction to DNA and depurination and/or depyrimidination (as discussed more fully hereinafter).

In one embodiment, it is preferred that the PAH be attached to Carbon-8, Nitrogen-3 or Nitrogen-7 of the purine base by a covalent bond to a reactive carbon of the PAH. The following formulas 1–3, A and B are illustrative:

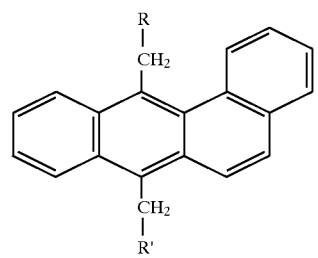

FORMULA 1 wherein R and R' can be hydrogen or a purine moiety selected from the group consisting of adenine or guanine. When R is hydrogen, R' is said purine moiety, and when R' is hydrogen, R is said purine moiety. Exemplary of the PAH-DNA adducts of FORMULA 1 are the following compounds:

7-(7-methylbenz[a]anthracene-12-methylen-yl)guanine, 7-(7-methylbenz[a]anthracene-12-methylen-yl)adenine, 7-(12-methylbenz[a]anthracene-7-methylen-yl)guanine, and 3-(12-methylbenz[a]anthracene-7-methylen-yl)adenine.

FORMULA 2

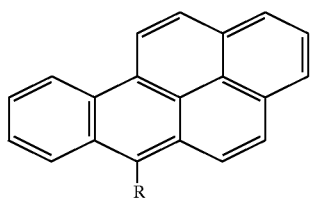

wherein R is adenine or guanine. The following compounds are exemplary:

7-(benzo[a]pyren-6-yl)guanine,
7-(benzo[a]pyren-6-yl)adenine, and
8-(benzo[a]pyren-6-yl)guanine.

FORMULA 3

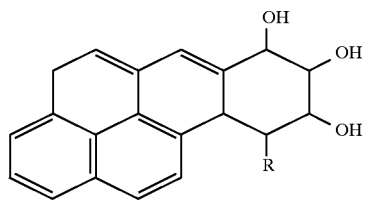

wherein R is adenine or guanine. The following compounds are exemplary:

7-(7,8,9-trihydroxy-7,8,9,10tetrahydrobenzo[a]pyren-10-yl)guanine, and
7-(7,8,9-trihydroxy-7,8,9,10tetrahydrobenzo[a]pyren-10-yl)adenine.

FORMULA A

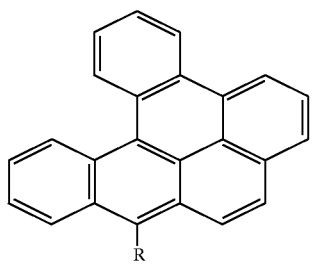

wherein R is adenine or guanine. The following compounds are exemplary:

7-(dibenzo[a,l]pyren-10-yl)guanine
7-(dibenzo[a,l]pyren-10-yl)adenine, and
8-(dibenzo[a,l]pyren-10-yl)guanine.

FORMULA B

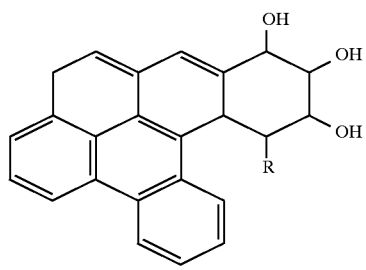

wherein R is adenine or guanine. The following compounds are exemplary:

7-(11,12,13-trihydroxy-11,12,13,14tetrahydrodibenzo[a,l]pyren-14-yl)guanine, and
7-(11,12,13-trihydroxy-11,12,13,14tetrahydrodibenzo[a,l]pyren-14-yl)adenine.

While exemplary compounds containing the purine bases are shown, the invention is also drawn to adducts formed using similar methods from PAH or HAH covalently linked to a pyrimidine base or nucleoside.

In addition to the above synthetic adducts, the present invention provides synthetic antigens useful in raising antibodies specific to the novel synthetic adducts of this invention. The antigen comprises a hapten, which is a synthetic adduct of this invention, covalently bound to an immunogenicity-conferring carrier, wherein, in the antigen molecule, all the functional groups of the hapten are free to exert their antigenic determinancy. Preferably, the carrier (generally a protein or polypeptide) is itself immunogenic, and a substantial plurality of hapten moieties are coupled to a single carrier moiety. The number of hapten molecules actually bound to the carrier is a function of the physical and chemical features of the carrier. As an example, for antigenically effective conjugates with native protein (polypeptide) carriers, the number of hapten moieties coupled to a single protein (polypeptide) molecule and the molecular weight of the protein (polypeptide) approximate a log/log relationship in which 1–5 haptens are coupled to a polypeptide of $10^3$ daltons, 5–10 haptens to a polypeptide of $10^4$ daltons, 25–30 haptens to a protein of $10^5$ daltons, 75–125 haptens to a protein of $10^6$ daltons, and 300–500 haptens to a protein of $10^7$ daltons. Exemplary are ovalbumin ($4.5 \times 10^4$ daltons), bovine serum albumin ($6.8 \times 10^4$ daltons) and keyhole limpet hemocyanin (4.5 to $13 \times 10^6$ daltons) coupled with 15–20, 20–25, and 300–500 hapten moieties, respectively.

Generally, in synthesizing the antigen, a linking agent is used. The linking agent can have two functional groups, the first to couple with the adduct, and the second to couple with the carrier. Generally, coupling of the linking agent to the adduct is through Amino-6 ($N^6$) or Carbon-2 (C-2) of adenine and Amino-2 ($N^2$) of guanine.

According to the present invention, a particular adduct target compound (ultimately to be assayed) is selected as a hapten to form an antigen which is then used to form antibodies for use in the immunochemical assay of adduct. In one embodiment these haptens can be represented by the structures of formulas 1–3 above.

Reference, hereinafter, to an "adduct" indicates a purine or pyrimidine base or nucleoside covalently linked to a polycyclic or heteropolycyclic aromatic hydrocarbon.

Thus, it is an object of the present invention to provide an antigen, and a method of producing it, which is capable of provoking the generation of antibodies specific to an adduct of this invention. Further objects reside in providing processes for preparing antigens and their corresponding antibodies, and in providing assays using these antibodies.

One method of the present invention encompasses preparing a synthetic antigen which is an adduct (hapten) coupled to a carrier. The method comprises the steps of derivatizing the synthetic adduct at the free amino functional group of the base moiety and coupling the derivatized adduct to the carrier. The carrier can be any macromolecule capable of conferring antigenicity, such as the protein keyhole limpet hemocyanin. In one example of this method, 7-(benzo[a]pyren-6-yl)guanine is derivatized at the $N^2$ position by reaction with 4-N-maleimidomethyl-cyclohexane-1-carboxylchloride (MCCCl) in dry pyridine to form an amide with the carbonyl moiety of MCCCl. This amide (derivatized adduct),

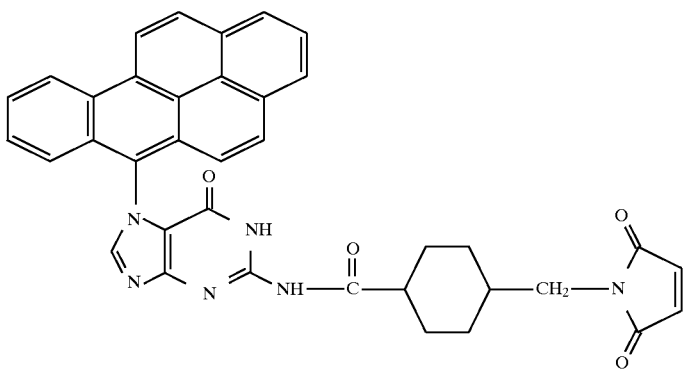

is purified to greater than 99% purity by a combination of normal phase and reverse phase chromatography, then dissolved in dimethylsulfoxide and added to a solution of Traut's modified keyhole limpet hemocyanin (KLH). In the latter, lysyl ε-amino groups have been converted to free sulfhydryl (SH) groups that react with the maleimido moiety of MCCCl to form a thioether bond coupling the derivatized adduct to the protein carrier (KLH). The antigenic adduct-carrier conjugates are separated from unreacted derivatized adduct by gel sieving chromatography.

Reaction sequences according to the invention generally are selective and give good yields. In particular, cross-reactions and isomer formation are not likely so that isolation of the antigen from antigenically distinct materials is not unduly difficult as the probability of other antigenic materials being formed is low.

Thus, the present invention further comprises antigens of the formula:

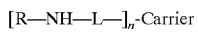

[R—NH—L—]$_n$-Carrier where "R—NH" represents an adduct of this invention exemplified by the adducts of Table 1; "L" is a linkage moiety between the carrier and the adduct at the 2-amino group of guanine or the 6-amino group of adenine or an amino group added to the C-2 of adenine, produced by the reaction of a first functional group of the linker (exemplified by the linkers in Table 1) with the adduct and a second functional group of the linker with the carrier; the "carrier" is a macromolecule (generally protein) conferring antigenicity; and "n" is an integer not exceeding the number of available reactive coupling groups on the carrier. Table 1 exemplifies adducts, linkers and carriers that may be used to produce functional antigens. Accordingly, the antigen of this invention is the product of coupling a linking agent with the carrier and with the free amino group of a nucleic acid base or nucleoside of the adduct, and "L" represents the resultant linkage connecting the carrier to the free amino group of the adduct.

In a preferred embodiment, "L" includes a cyclohexane ring and a one atom bridge between the cyclohexane ring and the adduct. The bridge can be organic or inorganic polyvalent atoms, for example, carbon, nitrogen or sulfur, carbon in the form of —C=O being especially preferred. The other side of the cyclohexane ring can be connected either directly or indirectly through, for example the maleimido ring to the second functional group of the linking agent which is coupled to the carrier.

In order to be capable of conferring antigenicity, the carrier will normally be antigenic itself, although it may be an incomplete antigen, becoming complete only when coupled to the hapten. To be antigenic, the carrier must be an immunogenic substance, that term being used to refer to a substance capable of eliciting production of antibodies in a host animal to which the immunogenic substance is administered. While, in general, it is believed that the terms "carrier" and "immunogenic substances" are clearly understood in the art, and the discussion herein is not meant to modify the ordinary significance of the terms, further definition is provided here for a clearer understanding of the development. The animal to which the antigenic substance is administered must be one having an effective immunologic system. The immunogenic substances must be "foreign" to the animal, in the sense of not being "self". That is, the immunogenic substance administered must not be one which is a natural body substance of the animal and would, therefore, be accordingly tolerated by the animal's immunologic system.

Generally, the antibodies elicited upon injection of the immunogenic substance into the animal will be generated by the host animal and will be capable of reacting or binding with the antigen in an observable and selective way. Thus, the antibodies will display some degree of discrimination between the administered immunogenic substance and other immunogenic materials.

The requirements for immunogenicity are not fully understood. However, it appears for a molecule to be antigenic, it must have a certain complexity and a certain minimal molecular weight. Formerly, it was thought that the lower molecular weight limit to confer antigenicity was about 5,000 da. However, antigenicity has recently been demonstrated with molecules having molecular weights as low as 2,000 da. Molecular weights of 3,000 da and more appear to be more realistic as a lower limit for immunogenicity, and approximately 6,000 da or more is preferred.

Exemplary immunogenic carrier materials are those set forth in Cremer et al., "Methods In Immunology" (1963), W. A. Benjamin Inc., New York, pages 65 to 113. That disclosure is herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyamino acid. An example of an apparently incomplete antigen is the polypeptide, glucagon.

A preferred class of natural carrier materials is the proteins. Proteins can be expected to have a molecular weight in excess of 5,000 da, commonly in the range of from 34,000 to 5,000,000 da. Specific examples of such natural proteins are bovine serum albumin (BSA), keyhole limpet hemocyanin (KLH), human gammaglobulin (HGG),-and thyroglobin.

Exemplary of synthetic carrier is the polyamino acid, polylysine. Where the synthetic antigen comprises a partially antigenic carrier conjugated with a hapten, it will generally be desirable for the conjugate to have a molecular weight in excess of 6,000 da, although somewhat lower molecular weights may be useful.

Preferably, the natural carrier has some solubility in water or aqueous alcohol. Desirably, the carriers are nontoxic to the animals to be used for generating antibodies.

The carrier must have one or preferably a plurality of functional moieties by means of which it can be coupled. Of course, these groups can be introduced synthetically. Preferably, in practicing the present invention, a single carrier moiety should have a plurality of hapten moieties coupled to it, for example, from about 20 to 40 for a protein of 100,000 da. In general, the maximum possible number of haptenic moieties per carrier molecule is preferred. Subject to steric hindrance and reduced structural complexity (and consequently reduced antigenicity), the maximum number will be determined by the number of reactive coupling groups on the carrier. For example, with BSA, it appears that the maximum number of hapten moieties that can be coupled is between 25 and 50.

In preparing the antigens of the invention it is, as a practical matter, very desirable to obtain them with a high degree of purity. High antigen purity appears to be an important requisite for optimum antibody production. Accordingly, it is desirable for the process to provide for isolation of the antigen from antigenically distinct materials. The latter will normally be undesired large molecules that may "confuse" the immune response of animals used for producing antibodies and are very difficult to separate from the desired antigen, even chromatographically. A feature of the process of the invention is that it is designed to minimize the formation of such undesired antigenically distinct materials.

However, as a general objective, it is desirable to ensure that the derivatized adduct compound is substantially purified for the carrier-coupling step, and is especially purified of substances that could covalently couple to the carrier under the intended conditions. Purification can, for example, be effected by chromatography or fractional crystallization, preferably to a degree of 98%.

Removal of small molecule reactants and reaction products from the synthesized antigen is generally desirable. However, some small molecule substances may be useful, for example for pH control. Thus, a convenient end-product form in which to recover the antigen is, in a buffered aqueous solution which is suitable for direct administration to animals.

The process of the invention can accordingly include a number of purification steps using well-known techniques such as column chromatography, dialysis and recrystallization. Further it will be generally desirable to use high purity reactants. For a natural protein carrier commercially available high purity fractions are desirable.

In addition to the above synthetic antigens, the present invention provides synthetic capture complexes useful in detecting and characterizing antibodies raised against the novel synthetic adducts of this invention, and in competitive enzyme-linked immunosorbent (ELISA) or other-solid phase immunoassays -that may be used in detection and quantitation of authentic adducts in biological samples. The capture complex comprises a hapten, which is a synthetic adduct of this invention, covalently bound to an adhesion molecule, wherein, in the capture complex, the functional groups of the hapten are free to exert their specific interaction and binding with antibodies directed against the novel adducts of this invention. Preferably, the adhesion molecule (generally a protein, polypeptide or polyamino acid) is not a component of the synthetic antigens which elicit antibodies to the novel adducts of this invention, and a substantial plurality of hapten moieties are coupled to a single adhesion molecule moiety. The number of hapten molecules bound to a single adhesion molecule may not be as high as the number of haptens bound to a single carrier in the synthetic antigens of this invention and may be as low as one molecule for each adhesion molecule. In one embodiment of the capture complex, 5 to 8 hapten moieties are bound to a single molecule of the protein bovine serum albumin.

Generally, in synthesizing the capture complex, a linking agent is used. The linking agent can have two functional groups, the first to couple with the adduct, and the second to couple with the adhesion molecule. Generally, coupling of the linking agent to the adduct is through the $N^6$ or C-2 of adenine or the $N^2$ of guanine.

According to the present invention, a particular adduct target compound (ultimately to be assayed) is selected as a hapten to form the capture complex which is then used to detect and characterize antibodies formed against the same hapten used to form the antigen. These haptens can be represented by the structures of formulas 1–3 above.

Thus, it is an object of the present invention to provide a capture complex, and a method of producing it, which is capable of interacting and binding specifically with the antibodies specific to an adduct of this invention. Further objects reside in providing processes for preparing capture complexes, and in providing assays using these capture complexes.

One method of the present invention encompasses preparing a synthetic capture complex which is an adduct (hapten) coupled to an adhesion molecule. For example, the method comprises the steps of derivatizing the synthetic adduct at the free amino functional group of a purine base moiety (or C-2 of adenine) and coupling the derivatized adduct to the adhesion molecule. The adhesion molecule can be any macromolecule capable of adhering to the solid phase of a solid phase immunoassay, such as the protein bovine serum albumin. In one example of this method, 7-(benzo[a]pyren-6-yl) guanine is derivatized at the $N^2$ position by reaction with 4-N-maleimidomethylcyclohexane-1-carboxylchloride (MCCCl) in dry pyridine to form an amide with the carbonyl moiety of MCCCl. This amide (derivatized adduct),

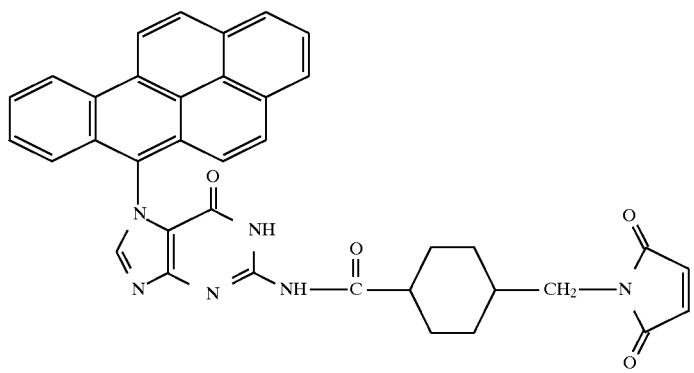

is purified to greater than 99% purity by a combination of normal phase and reverse phase chromatography, then dissolved in dimethylsulfoxide and added to a solution of Traut's modified bovine serum albumin (BSA). In the latter, lysyl ε-amino groups have been converted to free sulfhydryl (SH) groups that react with the maleimido moiety of MCCCl to form a thioether bond coupling the derivatized adduct to the adhesion molecule (BSA). The adduct-adhesion molecule conjugates are separated from unreacted derivatized adduct by gel sieving chromatography.

Reaction sequences according to the invention generally are selective and give good yields. In particular, cross-reactions and isomer formation are not likely so that isolation of the antigen-specific capture complex from antigenically distinct materials is not unduly difficult as the probability of other antigenic materials being formed is low.

Thus, the present invention further comprises capture complexes of the formula:

[R—NH—L—]$_n$-Adhesion Molecule where "R—NH" represents an adduct of this invention exemplified by the adducts of Table 1; "L" is a linkage moiety between the 2-amino group of guanine or the 6-amino group of adenine or an amino group added to the C-2 of adenine of the adduct and the adhesion molecule, produced by the reaction of a first functional group of the linker (exemplified by the linkers in Table 1) with the adduct and a second functional group of the linker with the adhesion molecule; the "adhesion molecule" is a macromolecule (generally protein) conferring adhesiveness to the solid phase of a solid phase immunoassay; and "n" is an integer not exceeding the number of available reactive coupling groups on the adhesion molecule. Table 1 exemplifies adducts, linkers and proteins that may be used to produce functional capture complexes. Exemplary of an immunogen for preparing monoclonal antibodies specific for 7-(benzo[a]pyren-6-yl)guanine is:

7-(Benzo[a]Pyren-6-yl)Guanine linked to KLH via Succinimidyl-4-Maleimidomethyl)Cyclohexane1-Carboxylate (300 mols adduct/mol KLH).

Exemplary of a capture complex for use in ELISAs for characterization of monoclonal antibodies specific for 7-(Benzo[a]Pyren-6-yl)Guanine and for detection of the adduct is:

7-(Benzo[a]Pyren-6-yl)Guanine linked to BSA via Succinimidyl-4-Maleimidomethyl)Cyclohexane-1-Carboxylate (8 mols adduct/mol BSA).

TABLE 1

| ADDUCT | LINKER | PROTEIN |
| --- | --- | --- |
| 7-(BENZO[A]PYREN-6-YL) GUANINE | SUCCINIMIDYL-4-(N-MALE-IMIDOMETHYL)CYCLOHEXANE-1-CARBOXYLATE | |
| 7-(BENZO[A]PYREN-6-YL) ADENINE | | OVA |
| 7-(DIBENZO[A,L]PYREN-10-YL) GUANINE | SULFOSUCCINIMIDYL-4-(N-MALEIMIDOMETHYL)CYCLO-HEXANE-1-CARBOXYLATE | BSA |
| 7-(DIBENZO[A,L]PYREN-10-YL) ADENINE | | THY |
| 7-(7-METHYLBENZ[A]-ANTHRACENE-12-METHYLEN-YL) GUANINE | N-γ-MALEIMIDOBUTYRYLOXY-SUCCINIMIDE ESTER | KLH |
| 7-(7-METHYLBENZ[A]-ANTHRACENE-12-METHYLEN-YL) ADENINE | N-γ-MALEIMIDOBUTYRYLOXY-SULFOSUCCINIMIDE ESTER | |
| 7-(7,8,9-TRIHYDROXY-7,8,9,10-TETRAHYDROBENZO[A]PYREN-10-YL)GUANINE | N-SUCCINIMIDYL-3-(2-PYRIDYLDITHIO)PROPIONATE | |

TABLE 1-continued

| ADDUCT | LINKER | PROTEIN |
|---|---|---|
| 7-(7,8,9-TRIHYDROXY-7,8,9,10-TETRAHYDROBENZO[A]PYREN-10-YL)ADENINE | | |

OVA = OVALBUMIN;
BSA = BOVINE SERUM ALBUMIN;
THY = THYROGLOBIN;
KLH = KEYHOLE LIMPET HEMOCYANIN.

Polyclonal antibodies can be raised by administration of an antigen of the invention to vertebrate animals, especially mammals such as goats or rabbits, using known immunization procedures. Usually a buffered solution of the antigen accompanied by Freund's adjuvant is injected subcutaneously at multiple sites. A number of such administrations at intervals of days or weeks is usually necessary. A number of animals, for example from 3 to 20, is so treated with the expectation that only a small proportion will produce good antibodies. However, one goat producing high quality antibodies in high titer can provide antibodies sufficient for thousands of assays. The antibodies are recovered from the animals after some weeks or months.

The use of monoclonal antibodies in the immunoassay embodiment of this invention is particularly preferred because they can be produced in large quantities and the product is homogeneous. The preparation of hybridoma cell lines for monoclonal antibody production derived by fusing an "immortal" cell line and lymphocytes sensitized against the immunogenic preparation can be done by techniques which are well known to those who are skilled in the art. See, for example, Doullard, J. Y. and Hoffman, T., "Basic Facts About Hybridomas" in Compendium of Immunology, vol. II, L. Schwartz (ed.) (1981); Kohler, G. and Milstein, C., Nature, 256:495–497 (1975); Koprowski, et al., European Journal of Immunology, 6:511–519; Koprowski et al., U.S. Pat. No. 4,172,124; Koprowski et al., U.S. Pat. No. 4,196,265; and Wands, U.S. Pat. No. 4,271,145; the teachings of which are herein incorporated by reference.

Unlike preparation of polyclonal sera, the choice of animal for monoclonal antibody production is dependent on the availability of appropriate "immortal" lines capable of fusing with lymphocytes thereof. Mouse and rat have been the animal of choice in hybridoma technology and preferably used. Humans can also be utilized as sources of sensitized lymphocytes if appropriate "immortalized" cell lines are available. For the purpose of the present invention, the animal of choice may be injected with approximately 0.1 mg to about 20 mg of a purified haptenic conjugate (antigen) of this invention. Usually the injecting material is emulsified in Freund's complete adjuvant. Boosting injections may also be required. The detection of antibody production can be carried out by testing the antisera with appropriately labeled antigen, as required by radioimmunoprecipitation, or with capture complex of this invention, as required by a variety of solid phase immunoassays including competitive ELISA. Lymphocytes can be obtained by removing the spleen or lymph nodes of sensitized animals in a sterile fashion and carrying out cell fusion. Alternatively, lymphocytes can be stimulated or immunized in vitro, as described, for example, in C. Reading, J. Immunol. Meth., 53:261–291, (1982).

A number of cell lines suitable for fusion have been developed, and the choice of any particular line for hybridization protocols is directed by any one of a number of criteria such as speed, uniformity of growth characteristics, absence of immunoglobulin production and secretion by the nonfused cell line, deficiency of metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: MPC sub 11-X45-6TG, P3-NS1-1-Ag4-1. P3-X63-Ag8, or mutants thereof such as X63-Ag8.653, SP2-O-Agl4 (all BALB/c derived), Y3-Agl.2.3 (rat) and U266 (human).

Cell fusion can be induced either by virus, such as Epstein-Barr or Sendai virus, or by polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1000 to 6000 da. It gives best results when diluted to about 20% to about 70% (w/w) in saline or serum-free medium. Exposure to PEG at 37 degrees C. for about 30 seconds is preferred in the present case, utilizing murine cells. Extremes of temperature (i.e., about 45 degrees C.) are avoided, and preincubation of each component of the fusion system at 37 degrees C. prior to fusion gives optimum results. The ratio between lymphocytes and malignant cells is optimized to reduce cell fusion among spleen cells and a range of from about 1:1 to about 1:10 (malignant cells:lymphocytes) gives good results.

The successfully fused cells can be separated from the myeloma line by any technique known in the art. The most common and preferred method is to choose a malignant line which is Hypoxanthine-Guanine Phosphoribosyltransferase (HGPRT) deficient, which will not grow in an aminopterin-containing medium used to allow only growth of hybrids and which is generally composed of hypoxanthine $1\times10^{-4}$M, aminopterin $4\times10^{-7}$M and thymidine $1.6\times10^{-5}$M, commonly known as HAT medium. The fusion mixture can be grown in the HAT-containing culture medium immediately after the fusion. Cell culture usually entails maintenance in HAT medium for one week and then feeding with either regular culture medium or hypoxanthine, thymidine-containing medium.

The growing colonies are then tested for the presence of antibodies that recognize the capture complex of this invention. Detection of hybridoma antibodies can be performed using an assay where the capture complex is bound to a solid support and allowed to react with hybridoma supernatants containing putative antibodies. The presence of antibodies may be detected by direct ELISA techniques using a variety of indicators. Most of the common methods are sufficiently sensitive for use in the range of antibody concentrations secreted during hybrid growth.

Cloning of hybrids can be carried out after approximately 21 days of cell growth in culture medium. Cloning can be performed by limiting dilution of cell cultures in fluid phase or by directly selecting single cells growing in semi-solid agarose. For limiting dilution, cell suspensions are diluted serially to yield a statistical probability of having less than one cell per well. For the agarose technique, hybrids are seeded in a semi-solid upper layer, over a lower layer of feeder cells. The colonies formed in the upper layer may be picked up and eventually transferred to microplate wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites fluid contains a higher concentration of monoclonal antibodies but includes high concentrations of serum proteins of the host animal Antibody purification may then be achieved by, for example, affinity chromatography. Alternatively, hybrids may be grown in high-output cell culture systems such as artificial capillary cartridges which generate monoclonal antibody concentrations comparable to those concentrations achieved in ascites fluid. It is possible to eliminate all protein supplements from such systems and thereby produce culture supernatants highly enriched for monoclonal antibodies that are easily purified.

The presence of the PAH or HAH adducts contemplated herein in an individual's serum, tissue, tissue extract or bodily excretion (urine) can be detected utilizing antibodies prepared as above, either monoclonal or polyclonal, in virtually any type of immunoassay. A wide range of immunoassay techniques are available, as can be seen by reference to U.S. Pat. Nos. 4,016,043; 4,424,279 and 4,018,653. These, of course, include both single-site and two-site (or "sandwich") assays of the non-competitive types, as well as the competitive binding assays.

Competitive assays are among the most useful and commonly used assays and are favored for use in the present invention. A number of variations of the competitive assay technique exist, and all are intended to be encompassed by the present invention.

Briefly, in a typical competitive assay, sample to be tested is brought into contact with a first antibody (i.e. an adduct-specific antibody of this invention). However, because most common assays are formulated for water-soluble haptens, the assays should be adapted to accommodate the hydrophobic nature of the adducts of the adducts being measured in the test sample. To illustrate, water-soluble haptens typically are combined directly with antibodies in a buffer that contains additional proteins, including serum albumin or other serum proteins, at a concentration-of about 1–10 mg/ml reaction mix. The presence of these additional proteins does not affect the binding of antibodies to water-soluble haptens, since they are dissolved in the aqueous medium and freely available for binding. By contrast, hydrophobic haptens tend to partition to hydrophobic domains of the additional proteins (e.g., each molecule of serum albumin possesses six large hydrophobic pockets), which interferes with their binding to antibodies in solution. Moreover, even in solutions having minimal additional protein, hydrophobic haptens tend to aggregate and precipitate from the reaction medium (this phenomenon increases with decreasing temperature).

To overcome the aforementioned difficulties associated with measuring hydrophobic haptens by competitive ELISA, several modifications have been developed in accordance with the present invention, which may be incorporated into standard ELISA techniques. These modifications are summarized below, and a specific embodiment of a competitive ELISA incorporating the modifications is described in Example 14.

First, antibody solutions should be prepared to eliminate substantially all extraneous (non-antibody) proteins. This modification enhances antibody/adduct interaction by eliminating the possibility that hydrophobic adducts will become sequestered in hydrophobic regions of non-antibody proteins. To accomplish this with monoclonal antibodies (MAbs), for example, hybridomas are grown in a low serum medium (approx. 2%) in a high production tissue culture system (preferably producing up to about 50 mg MAb/day). MAbs (or other antibodies) are purified by a two-step ammonium sulfate precipitation and by affinity chromatography on bioengineered Protein G ("protein A/G," Pierce, Rockford, Ill.). Additionally, conventional carrier/blocker proteins, such as BSA, are not included in the antibody/adduct reaction mixtures.

Second, Ethylene glycol (10–15% v/v) is incorporated into adduct/antibody reactions as a blocking agent instead of extraneous proteins. Ethylene glycol stabilizes antibodies (especially MAbs), and has been found to be a very effective blocking agent. This procedure eliminates uncontrolled non-specific binding of antibody that results from the low protein concentrations of reaction solutions, thereby permitting large antibody signals with a high signal/noise ratio.

Third, a detergent, preferably Tween 20 at 0.05% v/v, is incorporated into the reaction mixture to provide a simple matrix for maintaining the hydrophobic adduct in the aqueous environment (usually buffered saline). This modification has been found to reduce aggregation of the adducts and increase availability of the adducts to antibodies in the aqueous phase.

Fourth, the following general pre-treatment and incubation protocol should be used:

(1) antibody is diluted (approx. $1/500$–$1/5,000$, depending on specific binding affinity) in an aqueous solution (e.g., Tris/NaCl) which contains 10–15% ethylene glycol;

(2) diluted antibody is pre-heated at 50° C. for a suitable time period, (e.g., about 10 minutes), at which time gentle vortexing is initiated;

(3) adduct is added to the vortexing mix in a small volume (e.g., 10 ul in a typical reaction) methanol; and (4) mixtures are heated for an additional time period (e.g., 15 minutes) at 50° C., then held at 37° C. for a suitable incubation period, for a period of time sufficient to allow formation of immune complexes between adduct present in the sample and the first antibody (e.g., about 45 minutes), without further vortexing.

These reaction conditions increase the kinetic energy of both adduct and antibody, and disfavor aggregation of the adduct, thereby increasing availability of the adduct to antibody binding sites.

After completing the adduct/antibody incubations according to the modified procedures described above, the adduct/antibody mixture is incubated with unlabelled capture complex of this invention immobilized on a solid phase. Incubation is for a period of time sufficient to allow formation of binary complexes between free adduct-specific antibody (i.e. antibody that is not bound to free adduct of the test sample) and capture complex bound to the solid phase. Antibody that is not bound to capture complex as well as antibody that is bound to free adduct of the test sample is washed away, then a second antibody specific for the first antibody and labelled with a reporter molecule capable of producing a detectable signal is brought into contact with adduct-specific antibody (i.e. first antibody) bound to the capture complex. Incubation is for a period of time sufficient to allow formation of ternary complexes, i.e. capture complex-first antibody-second antibody. Any unreacted material is washed away and specific binding of the first antibody to capture complex is determined by observation of the signal produced by the reporter molecule. The presence of adduct in the sample tested is detected as a reduced signal in comparison with the signal generated by first antibody that has been incubated in test sample medium that does not contain adduct. Any adduct present in the test sample may be quantitated by comparing this signal reduction with signal-reduction produced by standard samples containing known amounts of adduct. Variations on the competitive assay include a simultaneous assay in which both sample and first antibody are simultaneously brought into contact with capture complex of this invention bound to a solid phase. These techniques are well known to those skilled in the art, and the possibility of minor variations will be readily apparent.

In the typical competitive assay, a capture complex, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid support may be in the form of tubes, beads, discs, or microplates, or any other surface suitable for conducting an immunoassay. The binding processes are well-known in the art and generally consist of cross-linking, covalently binding, or physically adsorbing the molecule to the insoluble surface. After capture complex binding, the polymer-capture complex is washed in preparation for a mixture of adduct-specific antibody, contemplated in this invention, and test sample containing the adduct. The adduct-specific antibody (first antibody) is incubated with test sample, at temperatures from 25 degrees C. to 60 degrees C., for a period sufficient to allow binding of adduct with the first antibody. The incubation period will vary but will generally be in the range of 2–40 minutes. After this incubation period, the solid phase with capture complex and bound first antibody is washed and incubated with a second antibody specific for the first antibody. The second antibody is linked to a reporter molecule which is used to indicate the binding of the first antibody to the capture complex. By "reporter molecule", as used in the present specification, is meant a molecule which, by its chemical nature, provides an analytically identifiable signal which allows the detection of antigen bound antibody. Detection may be either qualitative or quantitative. The most commonly used reporter molecules in this type of assay are either enzymes, fluorophores, or radioisotopes. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, among others. The substrates to be used with the specific enzymes are generally chosen for the production, upon hydrolysis by the corresponding enzyme, of a detectable color change. For example, p-nitrophenylphosphate is suitable for use with alkaline phosphatase conjugates; for peroxidase conjugates, 1,2-phenylenediamine, 5-aminosalicylic acid, or toluidine, are commonly used. It is also possible to use fluorogenic substrates, which yield a fluorescent product rather than chromogenic substrates noted above. In all cases, the enzyme-labelled antibody is added to the binary complex of first antibody and capture complex, allowed to bind, and then the excess reagent is washed away. A solution containing the appropriate substrate is then added to the ternary complex, i.e. capture complex-first antibody-second antibody. The substrate will react with the enzyme linked to the second antibody, giving a detectable signal which may be quantitated, usually spectrophotometrically, to give an indication of the amount of first antibody bound. Reduction of this signal in comparison with the signal produced by first antibody that has not been reacted with adduct in the test sample is an indication of the presence of the adduct in the test sample. Adduct in the test sample may be quantitated by comparing signal reduction due to incubation of the first antibody with the test sample, to signal reduction due to incubation of the first antibody with known amounts of adduct.

Alternatively, fluorescent compounds, such as fluorescein and rhodamine, may be chemically coupled to antibodies without altering their binding capacity. When activated by illumination with light of a particular wavelength, the fluorochrome absorbs the light energy, inducing a state of excitation in the molecule, followed by emission of light at a characteristic wavelength detectable with a spectrofluorometer or other similar instrument. As in the enzyme-linked assay (EIA), the fluorochrome-labelled second antibody is allowed to bind to the binary complex consisting of first antibody bound to capture complex. After washing away the unreacted reagent, the remaining ternary complex is then exposed to light of the appropriate wavelength, and the fluorescence observed indicates binding of the first antibody to the capture complex. Again, signal reduction is an indication of adduct present in the test sample. Immunofluorescence and EIA are both very well established in the art and are particularly preferred for the present method. However, other reporter molecules, such as radioisotopes, chemiluminescent or bioluminescent molecules, may be employed. It will be readily apparent to the skilled technician how to vary the procedure to suit the required purpose. It will also be apparent that the foregoing can be used to detect the adducts of this invention.

Accordingly,the present invention is also directed to a kit for the rapid and convenient assay of PAH-DNA or HAH-DNA adducts in mammalian body fluids (e.g. serum, tissue extracts, tissue fluids), mammalian excreta (e.g. urine), in vitro cell culture supernatants, and cell lysates. The kit is compartmentalized to receive a first container adapted to contain a capture complex of this invention, a second container adapted to contain the first antibody (adduct-specific antibody) and the test sample containing the adduct, and a third container adapted to contain a second antibody specific for the first antibody, said second antibody being labelled with a reporter molecule capable of giving a detectable signal as hereinbefore described. If the reporter molecule is an enzyme, then a fourth container adapted to contain a substrate for said enzyme is provided. In an exemplified use of the subject kit, a sample to be tested for adduct is contacted with the contents of the second container for a time and under conditions for PAH-DNA or HAH-DNA adduct, if present, to bind to the antibodies contained in said second container. The contents of this second container are contacted with the contents of the first container. If antibodies of the second container have not bound to free adduct of the sample, said antibodies have the opportunity to bind to capture complex in the first container to form a binary complex between first antibody and capture complex.

Unreacted antibody is washed from the first container, then the labelled antibodies of the third container are contacted with the residue in the first container. If antibodies of the second container have bound to capture complex of the first container, the antibodies of the third container bind to the binary complex and, since said second antibodies are labelled-with a reporter molecule, when subjected to detecting means, the tertiary complex is detected. The amount of adduct in the test sample is detected as a reduction of the signal produced by incubation of the first antibody with test sample in comparison with the signal produced by incubation of the first antibody in the absence of adduct. A fifth container is adapted to contain standard adduct, to be diluted with sample medium and contacted with first antibody of the second container. Signal reduction by the test sample is compared with signal reduction by the adduct standards and determines the amount of adduct in the test sample.

Polycyclic Aromatic Hydrocarbon-Nucleoside Adducts

As discussed previously, new, chemically-pure compositions of matter which are adducts of DNA nucleosides and PAH or HAH are herein provided. Methods for the synthesis and isolation of these novel adducts are hereinafter decribed.

A mechanism of adduction is described in which reactive intermediates are formed by anodic oxidation and react with various nucleophilic groups of deoxyadenosine and deoxyguanosine. For example, anodic oxidation of 7,12-dimethylbenz[a]anthracene (DMBA) in the presence of deoxyguanosine yields four adducts: 7-methylbenz[a]-anthracene(MBA)-12-$CH_2$-C8dG (13%), 7-MBA-12-$CH_2$-N7Gua (55%), 12-MBA-7-$CH_2$-N7Gua (12%), and 7-MBA-12-$CH_2$-C8Gua (10%). The first three are primary products of the electrochemical reaction, whereas the last one is a secondary product. Binding occurs predominantly at the 12-$CH_3$ group of DMBA and specifically to the N-7 and C-8 of guanine. On the other hand, anodic oxidation of DMBA in the presence of deoxyadenosine gives only two detectable adducts: 7-MBA-12-$CH_2$-N7Ade (45%) and 12-MBA-7-$CH_2$-N3Ade (55%). Binding at the 12-$CH_3$ group is specific for the N-7 of Ade, whereas the 7-$CH_3$ group of DMBA is specific for the N-3 of Ade.

In a second synthetic route, anodic oxidation of benzo[a]pyrene (BP) in the presence of deoxyguanosine yields four adducts: 7-(BP-6-yl)Gua ("BP-6-N7Gua", 46% yield); 8-(BP-6-yl)Gua ("BP-6-C8Gua", 14.5% yield); $N^2$-(BP-6-yl)dGua ("BP-6-$N^2$dG", 6% yield), and 3-(BP-6-yl)dG ("BP-6-N3dG", 3% yield). Anodic oxidation of BP in the presence of deoxyadenosine yields one adduct, 7(BP-6-yl)Ade ("BP-6-N7Ade", 5% yield).

In the third and last route, reaction of benzo[a]pyrene-7,8-dihydrodiol-9,10-epoxide with deoxyguanosine produces 10-(guanin-7-yl)-7,8,9trihydroxy-7,8,9,10-tetrahydrobenzo[a]pyrene ("BPDE10-N7Gua") in 64% yield, and reaction with deoxyadenosine produces 10-(adenin-7-yl)-7,8,9trihydroxy-7,8,9,10-tetrahydrobenzo[a]pyrene ("BPDE10-N7Ade") in 36% yield.

Structures of the aforementioned adducts were elucidated by NMR.

Chemical Synthesis of Polycyclic Aromatic Hydrocarbon-Nucleotide Adducts

In addition to electrochemically synthesized adducts, the present inventors have discovered that adducts can be synthesized chemically. A new method of adduction is described in which reactive intermediates of PAH or HAH formed by oxidation with iodine react with various nucleophilic groups of deoxyadenosine, deoxyguanosine, adenine, guanine, deoxycytosine, deoxythymidine, thymidine or cytosine. For example, oxidation of 7,12 dimethylbenz[a]anthracene (DMBA) by iodine in the presence of deoxyguanosine-yields four adducts: 7methylbenz[a]anthracene (MBA)-12$CH_2N^2$dG and 12-MBA-7$CH_2N^2$dG (15% yield), and 7-MBA-12$CH_2$-N7Gua and 12-MBA-7$CH_2$-N7Gua (25% yield). Oxidation of DMBA by iodine in the presence of deoxyadenosine gives 7-MBA-12-$CH_2$-N7 Ade in 11% yield and 12-MBA-7$CH_2$-N7Ade in 32% yield. Oxidation of DMBA by iodine in the presence of adenine gives 7-MBA-12-$CH_2$-N7 adenine in 23% yield and 12-MBA7$CH_2$-N7 adenine in 48% yield.

In a second example, oxidation of benzo[a]pyrene (BP) in the presence of deoxyguanosine gives BP-6-N7Gua in a yield of 45%. Oxidation of BP in the presence of deoxyadenosine give BP-6N7Ade in a 5% yield. When BP is oxidized by iodine in the presence of adenine, three products are obtained, BP6N1Ade, BP-6N3Ade and BP-6N7Ade in yields of 76%, 4% and 2% respectively.

Definitions:

A number of terms and expressions are used throughout the specification and claims. In order to assure uniformity and avoid ambiguity, the following definitions are provided:

The term "polycyclic aromatic hydrocarbon(s)" (PAH) is intended to cover any PAH found in the environment. The term "heteropolycyclic aromatic hydrocarbon(s)" (HAH) is intended to cover any HAH found in the environment. These compounds are well known and have been described in the literature. (For example see Grimmer at page 3 above. Generally, these compounds have been artificially introduced into the environment as a result of incomplete combustion of organic substances. They are found in tobacco smoke and in other atmospheric pollutants, for example, from industrial sources, in particular, petroleum refineries, chemical-manufacturing facilities, steel manufacturing facilities, electrical generating plants fueled by fossil fuels, and the like. The PAH(s) of this invention must be capable of adduction to DNA and depurination (as defined hereinafter). Exemplary of such PAHs are benzo[a]pyrene (BP); 7,12-dimethylbenz[a]anthracene (DMBA); and dibenzo[a,l]pyrene (DB[a,l]P). An exemplary HAH of the invention is 7-H-dibenzo[c,g]carbazole (DBC).

By the term "adduct" as used herein is meant the covalent linkage of a PAH molecule or HAH molecule to a purine nucleoside or base or a pyrimidine nucleoside or base in a DNA molecule.

By the term "depurination" is meant the metabolic removal of a purine-base adduct (as herein defined) from a DNA strand in which it was generated, leaving in its place an open (apurinic) site on the sugar-phosphate backbone. Those adducts which are susceptible to depurination are described as being "depurination" adducts; those which remain bound to the DNA strand are described as being "stable" adducts.

By the term "depyrimidination" is meant the metabolic removal of a pyrimidine-base adduct (as herein defined) from a DNA strand in which it was generated, leaving in its place an open (apyrimidinic) site on the sugar-phosphate backbone. Those adducts which are susceptible to depyrimidination are described as being "depyrimidination" adducts; those which remain bound to the DNA strand are described as being "stable" adducts.

Figure 1:
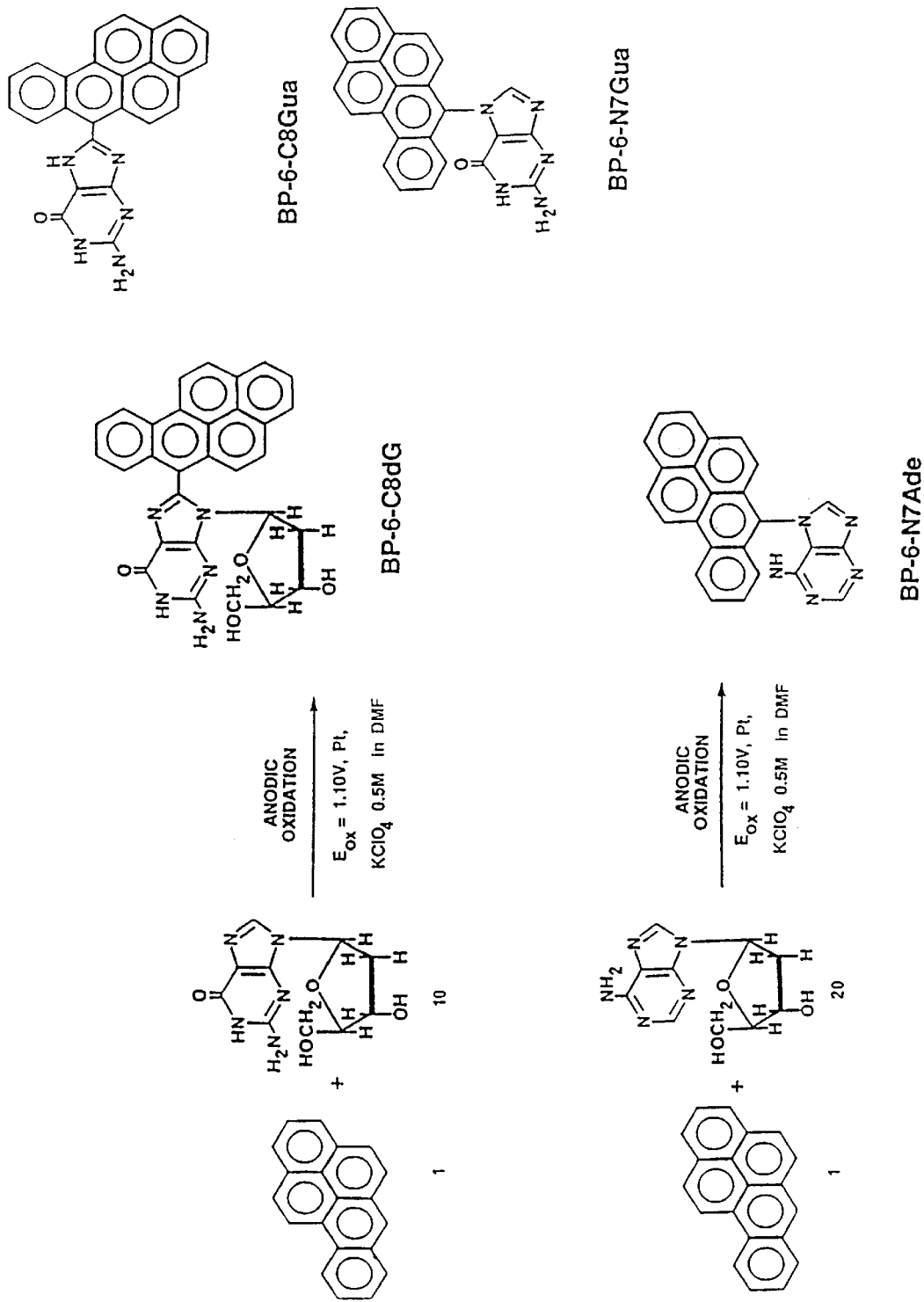
FIG. 1. Electrochemical oxidation of BP in the presence of deoxyguanosine or deoxyadenosine.

Certain essential materials and in vitro methods were utilized in preparing the several PAH adducts described in the present invention. A detailed description of the preferred materials and methods used to produce these adducts is presented below in EXAMPLE 1.

EXAMPLE 1

Preferred Materials and Methods Used in the In Vitro-Synthesis of PAH-Nucleoside Adducts Chemicals Benzo[a]pyrene (BP) was obtained from Sigma Chemical Company (St. Louis, Mo.), or from Aldrich Chemical Company, Inc., (Milwaukee, Wis.), and was purified by column chromatography on aluminum oxide eluted with benzene/hexane (1:1). The BP product was then recrystallized from the benzene/hexane solvent, and had a melting point (m.p.) of 177°–178° C. [$^{14}$C]BP (52 mCi/mmol) was purchased from Amersham (Arlington Heights, Ill.). Commercially-supplied (Sigma, Aldrich) 7,12-dimethylbenz[a]anthracene (DMBA) was purified by column chromatography on silica gel by eluting with benzene/hexane (1:1) and recrystallization from benzene/methanol (m.p. 121°–122° C.).

Benzo[a]pyrene-trans-7,8-dihydrodiol-9,10-epoxide (anti) (BPDE) (m.p. 205°–207° C.) was obtained from the National Cancer Institute Chemical Carcinogen Repository, Bethesda, Md. It was more than 98% pure and was used without further processing. Guanosine (G) and adenosine (A), and the deoxynucleosides deoxyguanosine (dG), deoxycytidine (dC), deoxythymidine (dT), deoxyadenosine (dA), were purchased from Aldrich or Sigma Chemical Company, and were desiccated over phosphoric anhydride ($P_2O_5$) under vacuum at 110° C. for 48 hours prior to use.

Commercially available dimethylformamide (DMF) (Aldrich Chemicals) was purified by refluxing over calcium hydride ($CaH_2$), followed by vacuum distillation just prior to use, and was stored over 4-Angstrom molecular sieves under argon. Potassium perchlorate ($KClO_4$) was used as obtained from Aldrich Chemicals.

Ultraviolet (UV) Absorbance Spectra

UV absorbance spectra were recorded with a Waters 990 photodiode array detector during high pressure liquid chromatography (HPLC) in $CH_3OH/H_2O$ or $CH_3CN/H_2O$ gradients.

Nuclear Magnetic Resonance (NMR)

Proton and homonuclear two-dimensional chemical shift correlation spectroscopy (COSY), and Nuclear Overhauser Effect (NOE) nuclear magnetic resonance spectra, were recorded on a Varian XL-300 instrument at 299.938 Mhz in dimethylsulfoxide (DMSO)-d6 at 30° C. Chemical shifts ("delta") were reported relative to tetramethylsilane, which was employed, as needed, either as a primary internal reference or as a secondary reference relative to DMSO at 2.50 ppm, and the J values were given in Hertz. Typical instrument parameters were as previously reported (Rogan et al., *J. Amer. Chem. Soc.* 110: 4023, 1988).

NOE Difference Spectra

NOE difference spectra were recorded by applying a presaturation pulse with a decoupler on resonance, and subtracting the trace from the corresponding reference spectra recorded under identical conditions but with the decoupler off resonance. Typical spectra were obtained from at least 2560 transients.

High-Pressure Liquid Chromatography (HPLC)

HPLC was conducted on a Waters 600E solvent delivery system equipped with a Waters 700 WISP autoinjector. Effluents were monitored for UV absorbance (254 nanometer wavelength) with a Waters 990 photodiode array detector, and the data were collected on an APC-IV Powermate computer. Analytical runs were conducted on a YMC (YMC, Overland Park, Kans.) ODS-AQ 5-micrometer, 120-Angstrom column (6.0×250 millimeters) with a flow rate of 1 mL/minute. After the column was eluted for 5 minutes with 30% $CH_3CN$ in $H_2O$, a 70-minute curvilinear gradient (CV7) to 100% $CH_3CN$ was run at 1 mL/minute. Preparative HPLC was conducted on a YMC ODS-AQ 5-micrometer, 120-Angstrom column (20×250 millimeters) at a flow rate of 6 mL per minute. Both $CH_3OH/H_2O$ and $CH_3CN/H_2O$ gradients were used, depending upon the experiment.

Electrochemical Synthesis of Adducts

Electrochemical syntheses were conducted with an apparatus such as the instrument provided for this purpose by EG & G Princeton Applied Research (Princeton, N.J.), as previously described (Rogan et al., *J. Amer. Chem. Soc.* 110: 4023, 1988).

The electrolysis potential for BP or DMBA was selected on the basis of its anodic peak potential as measured by cyclic voltammetry, using a Model CV27 supplied by Bioanalytical Systems (Lafayette, IN). The oxidation potential used for the synthesis of BP or DMBA adducts was 1.10 volts, which was slightly less than their anodic peak potentials of 1.12 or 1.20 volts, respectively.

All glassware, syringes, needles, electrochemical cell, platinum working and reference electrodes were oven-dried at 150° C. prior to use. The electrochemical cell and working electrode were assembled while hot and then cooled under argon.

The electrochemical reactions of BP or DMBA with various nucleosides were conducted as reported earlier (Rogan et al., *J. Amer. Chem. Soc.* 110: 4023, 1988). Both the output current ("i") and the total charge ("Q") were monitored throughout the experiment. The reaction was stopped when "i" had decreased to about ½₀th of the initial value and a charge three times the theoretical charge expected (for a two-electron transfer) had accumulated; these two conditions were usually achieved in about 90 minutes.

Purification of electrochemical products

A major objective of the present invention was achieved by the following novel methodology which accomplished, with one procedure, the purification of all of the electrochemical reaction products of the present invention.

When the aforementioned electrochemical synthetic reactions were complete, DMF was removed under vacuum. The various adducts were extracted four times from solid potassium perchlorate by using a solvent mixture of ethanol/chloroform/acetone in a volume-to-volume ratio of 2:1:1. The resulting extract was filtered through a Whatman fluted filter paper. The combined solvent mixture was evaporated under vacuum, the residue was dissolved in 3 mL of DMSO, filtered through a DMSO-resistant 0.45 micron filter, and analyzed by HPLC with a $CH_3CN/H_2O$ or $CH_3OH/H_2O$ gradient. Purification of the isolated adducts was done by preparative HPLC in $CH_3OH/H_2O$, followed by a $CH_3CN/H_2O$ gradient. In contrast to previous methods of purification, the new method herein described was used to purify all of the adducts of the present invention. The new method enables one to achieve much higher yields of adducts in much shorter times than the previous method did.

Synthesis of Adducts by Iodine Oxidation

PAH (0.1 mmol) or HAH (0.1 mmol) and nucleoside or base (5 mmol) (adenine, thymidine, cytosine, guanine, uracil) were placed in a dry three necked flask and dissolved in 3.5 ml of an aprotic solvent, dimethylformamide (DMF) or dimethylsulfoxide (DMSO). Iodine (0.3 mmol in 1.5 ml of DMF or DMSO) was slowly added to this solution under stirring. The mixture was reacted for 1 hour at room temperature, in some instances, silver perchlorate (0.1 mmol in 2.5 ml of DMF or DMSO) was then slowly added with stirring. The reaction was continued overnight, with or without silver perchlorate. The excess iodine was then reduced with sodium thiosulfate and the solvent removed under vacuum. The adducts were extracted three times by using a solvent mixture of ethanol/chloroform/acetone in a volume to volume ratio of 2:1:1. The resulting extract was filtered through a Whatman fluted filter paper and then evaporated under vacuum. The residue was dissolved in 3 ml of DMSO, filtered through a DMSO-resistant 0.45 Am filter. The isolated adducts were purified by preparative HPLC with a methanol/water gradient, followed by an acetonitrile/water gradient, and identified by nuclear magnetic resonance.

Having described in this example the preferred methods and materials used to produce the novel PAH-nucleoside or HAH nucleoside adducts of the present invention, the remaining examples will further demonstrate the manner in which the present invention may be practiced.

EXAMPLE 2

Adducts Produced in the Reaction of BP and Deoxyguanosine

FIG. 1 is a diagrammatic summary of the synthesis of several BP adducts by one-electron oxidation. When the electrochemical reaction of BP and deoxyguanosine (1:10 molar ratio) was conducted with the consumption of 8 equivalents of charge (29 Coulombs), four adducts were obtained, BP-6-C8Gua (14.5%), BP-6-N3dG (3%), BP-6-$N^2$dG (6%), and BP-6-N7Gua (46%), with 10% unreacted BP. Under these conditions, all of the BP-6-C8dG initially produced was completely converted to BP-6-C8Gua and the reaction produced, in small yield, two new adducts of the present invention, BP-6-N3dG and BP-6-$N^2$dG. The products were analyzed by HPLC by eluting the column with 30% $CH_3OH$ in $H_2O$ for 5 minutes, followed by a linear gradient to 100% $CH_3OH$ in 75 minutes at a flow rate of 1 mL per minute. The adducts were then purified by preparative HPLC and their structures were determined by NMR.

The NMR data for BP-6-C8dG, BP-6-C8Gua and BP-6-N7Gua have already been published (Rogan et al., *J. Amer. Chem. Soc.* 110: 4023, 1988). Following are NMR data for BP-6-N3dG and BP-6-$N^2$dG.

BP-6-N3dG: Structure, Ultraviolet and NMR spectra

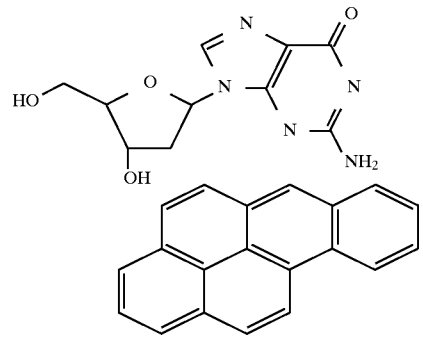

Figure 2:
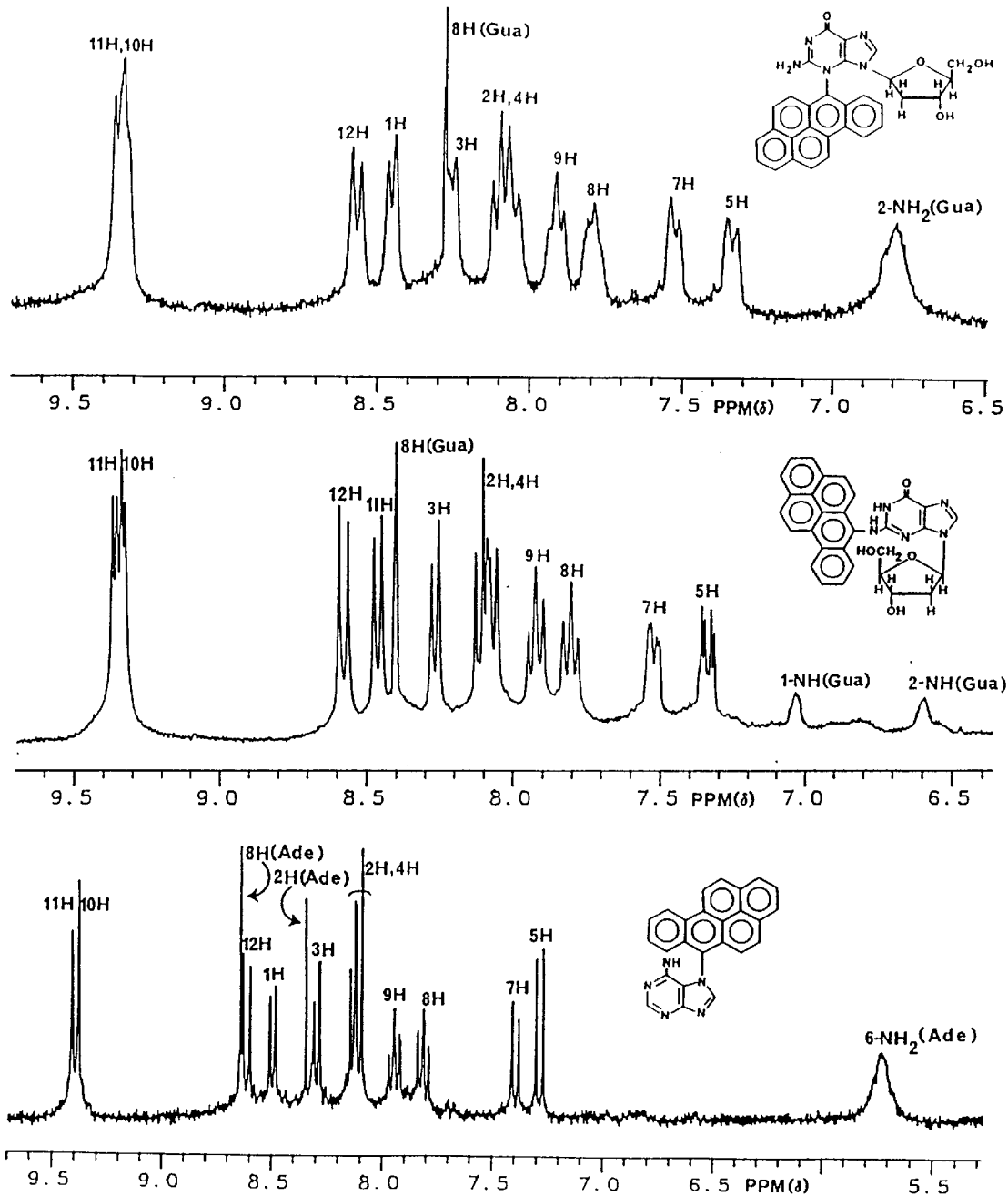
FIG. 2. NMR spectra of A) BP-6-N3dG; B) BP-6-$N^2$dG; and C) BP-6-N7Ade.

UV, absorbance wavelength maximum (in nanometers), 254, 266, 286, 302, 357, 374, 395, 408;
NMR, 1.75 (m, 2H, 2'$H_2$), 3.45–3.53 (m, 3H, 4'-H, 5'$H_2$), 3.80 (m, 1H, 3'-H), 5.42 (m, 1H, 1'-H), 6.80 (bs, 2H, 2-$NH_2$[Gua]), 7.33 (d, 1H, 5-H), 7.53 (d, 1H, 7-H), 7.81 (t, 1H, 8-H), 7.92 (t, 1H, 9-H), 8.05 (d, 1H, 4H), 8.11 (t, 1H, 2-H), 8.26 (d, 1H, 3-H), 8.30 (s, 1H, 8-H[Gua]), 8.45 (d, 1H, 1-H), 8.57 (d, 1H, 12-H), 9.31–9.40 (m, 2h, 10-H, 11-H). The spectrum is shown in FIG. 2A.

BP-6-$N^2$dG: Structure, Ultraviolet and NMR spectra

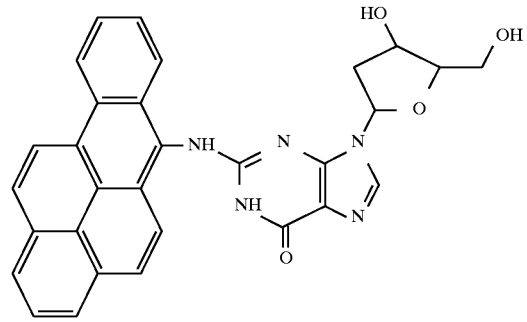

UV, wavelength absorbance maximum (in nanometers), 254, 266, 286, 302, 357, 374, 395, 408;
NMR, 1.65–1.85 (m, 2H, 2'-$H_2$), 3.50–3.62 (m, 2H, 5'$H_2$), 3.65–3.95 (m, 2H, 3'-H, 4'-H), 5.39 (t, 1H, 1'-H), 6.65 (bs, 1H, 2-NH[Gua]), 7.09 (bs, 1H, 1-NH[Gua]), 7.38 (d, 1H, 5-H), 7.56 (d, 1H, 7-H), 7.85 (t, 1H, 8H), 7.96 (t, 1H, 9-H), 8.08 (d, 1H, 4-H), 8.13 (d, 1H, 2-H), 8.30 (d, 1H, 3-H), 8.43 (s, 1H, 8-H[Gua]), 8.50 (d, 1H, 1-H), 8.63 (d, 1H, 12-H), 9.35–9.45 (m, 2H, 10-H, 11-H). The spectrum is shown in FIG. 2B.

EXAMPLE 3

Reaction of BP and Deoxyadenosine (dA)

The reaction procedure for the coupling of BP radical cation with deoxyadenosine (dA) is the same as that of BP radical cation and deoxyguanosine (dG), as previously reported (Rogan et al., *J. Amer. Chem. Soc.* 110: 4023, 1988). When the reaction was conducted at a molar ratio of BP:dA equal to 1:10, however, no appreciable amounts of adducts were formed, even with the consumption of 5 equivalents of charge. However, the reaction succeeded when the molar ratio of BP to dA was changed to 1:20 and the charge consumed was 5.8 equivalents (22.2 Coulombs). This afforded only one adduct, BP-6-N7Ade (5%). The availability of this new synthetic adduct has for the first time permitted identical biologically-produced adducts to be detected in clinical specimens such as, for example, urines.

BP-6-N7Ade: Structure, Ultraviolet and NMR spectra

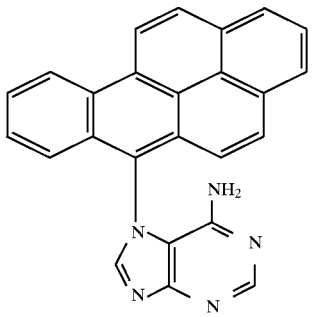

UV, absorbance wavelength maximum (in nanometers), 256, 267, 288, 302, 357, 377, 396, 407;

NMR, 5.70 (bs, 2H, 6-NH2[Ade]), 7.32 (d, 1H, 5-H), 7.44 (d, 1H, 7-H), 7.85 (t, 1H, 8-H), 7.99 (t, 1H, 9H), 8.14 (d, 1H, 4-H), 8.18 (d, 1H, 2-H), 8.33 (d, 1H, 3-H), 8.39 (s, 1H, 2-H[Ade]), 8.54 (d, 1H, 1-H), 8.65 (d, 1H, 12-H), 8.68 (s, 1H, 8-H[Ade]), 9.43 (m, 2H, 10-H, 11-H). The spectrum is shown in FIG. 2C.

EXAMPLE 4

Adducts Produced In Vitro in Reactions with 7,12-dimethylbenz[a]anthracene (DMBA)

The adducts of DMBA with deoxyguanosine and deoxyadenosine were prepared and purified by the procedures described in detail in EXAMPLE 1 above.

Figure 3:
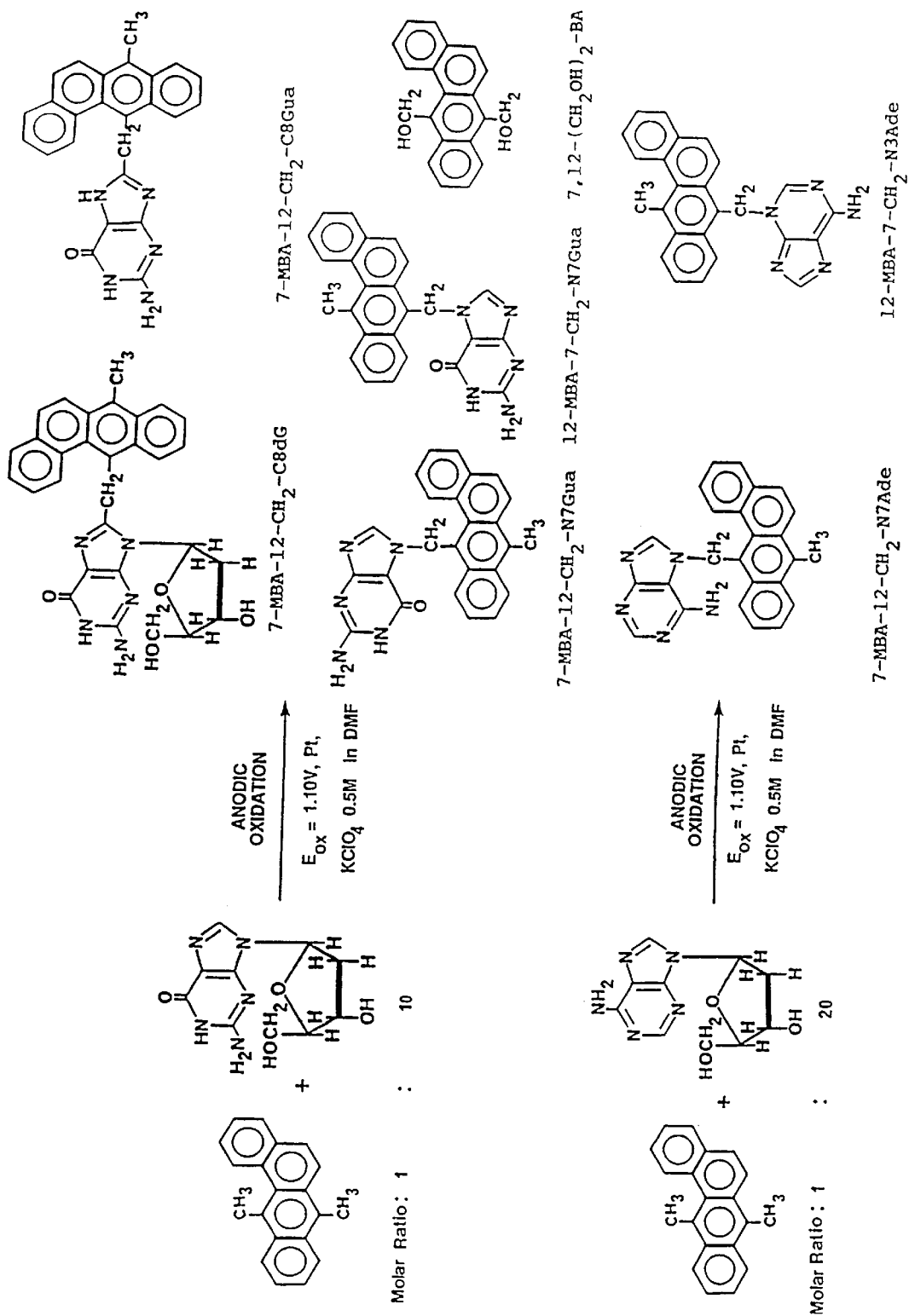
FIG. 3. Electrochemical oxidation of DMBA in the presence of deoxyguanosine or deoxyadenosine.
Figure 4:
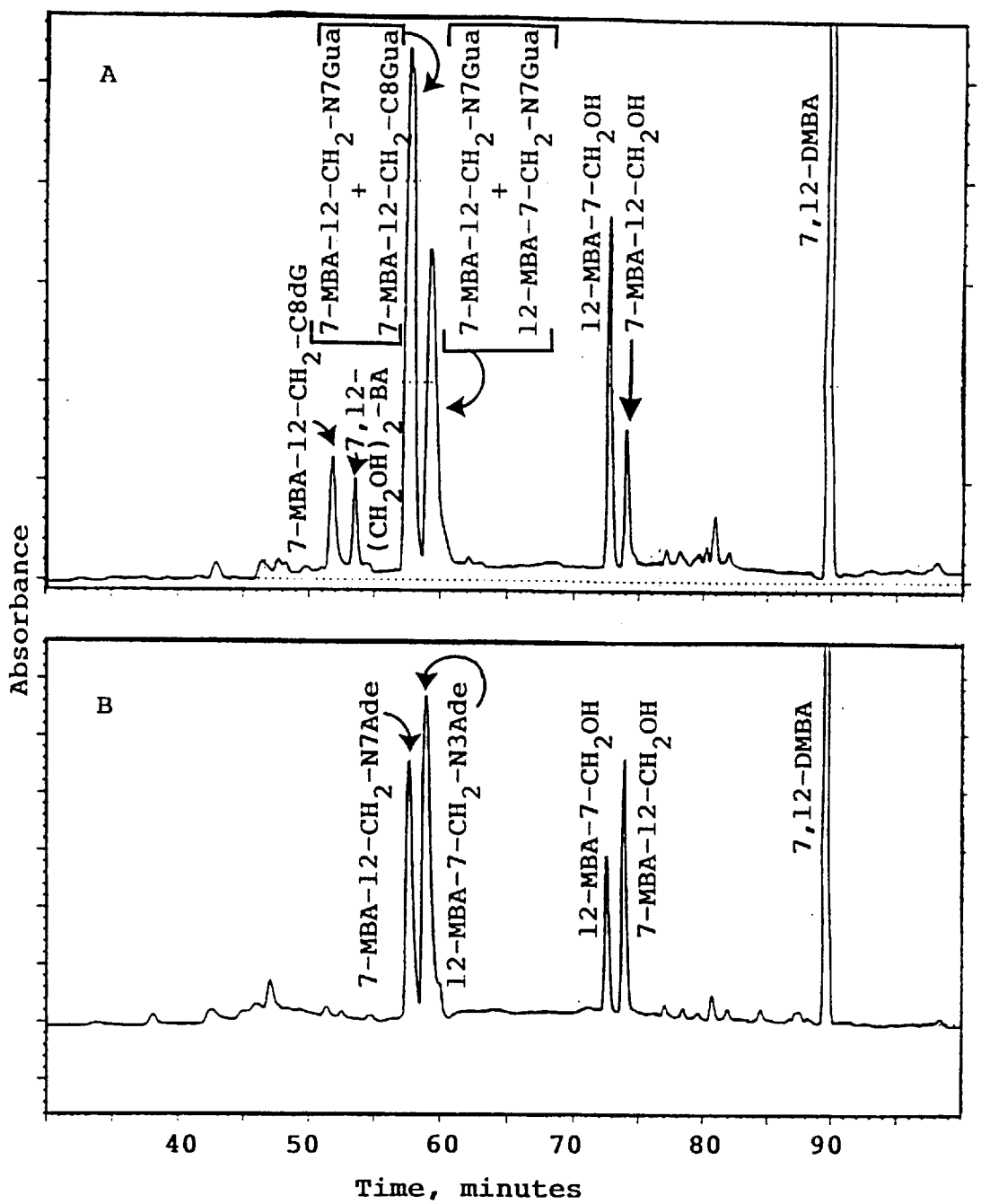
FIG. 4. HPLC separation of the products obtained by electrochemical oxidation of DMBA in the presence of A) deoxyguanosine (dG), or B) deoxyadenosine (dA).

The isolated products from the DMBA and deoxyguanosine reaction were 7-MBA-12-CH$_2$-C8dG (13%), 7,12-(CH$_2$OH)$_2$-BA (10%), 7-MBA-12-CH$_2$-C8Gua (10%), 7-MBA-12-CH$_2$-N7Gua (55%) and 12-MBA-7-CH$_2$-N7Gua (12%) (FIG. 3). The reaction between DMBA and deoxyadenosine gave two products: 7-MBA-12-CH$_2$-N7Ade (45%) and 12-MBA-7-CH$_2$-N3Ade (55%) (FIG. 3). That two of the aforementioned adducts, 7-MBA-12-CH$_2$-N7Gua and 7-MBA-12-CH$_2$-N7Ade are formed biologically is demonstrated for the first time in the present invention.

Structures of the six newly-synthesized adducts, elucidated by using proton NMR, with the support of COSY and NOE spectra, follow.

7-MBA-12-CH$_2$-C8dG: Structure, Ultraviolet and NMR spectra

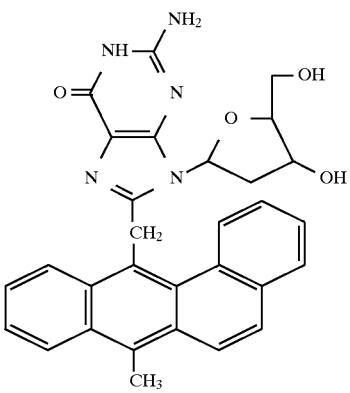

UV, absorbance wavelength maximum (nanometers) 224, 250, 294, 304, 368, 384;

NMR, 2.11 (m, 1H, 2'-H), 2.65 (m, 1H, 2'-H), 3.05 (s, 3H, 7-CH$_3$), 3.43 (m, 2H, 5'-H2), 3.68 (m, 1H, 4'-H), 4.26 (m, 1H, 3'-H), 4.90 (bs, 1H, 5'-OH), 5.09 (bs, 1H, 3'-OH), 5.19 (s, 2H, 12-CH$_2$), 6.10 (t, 1H, 1'-H), 7.48 (t, 1H, 3-H), 7.53 (t, 1H, 2-H), 7.59–7.75 (m, 5H, 5-H, 9-H, 10-H, 2-NH$_2$ [Gua]), 7.88 (d, 1H, 4-H), 8.09 (d, 1H, 6-H), 8.29 (d, 1H, 11-H), 8.41 (d, 1H, 8-H), 8.59 (d, 1H, 1-H).

Figure 5:
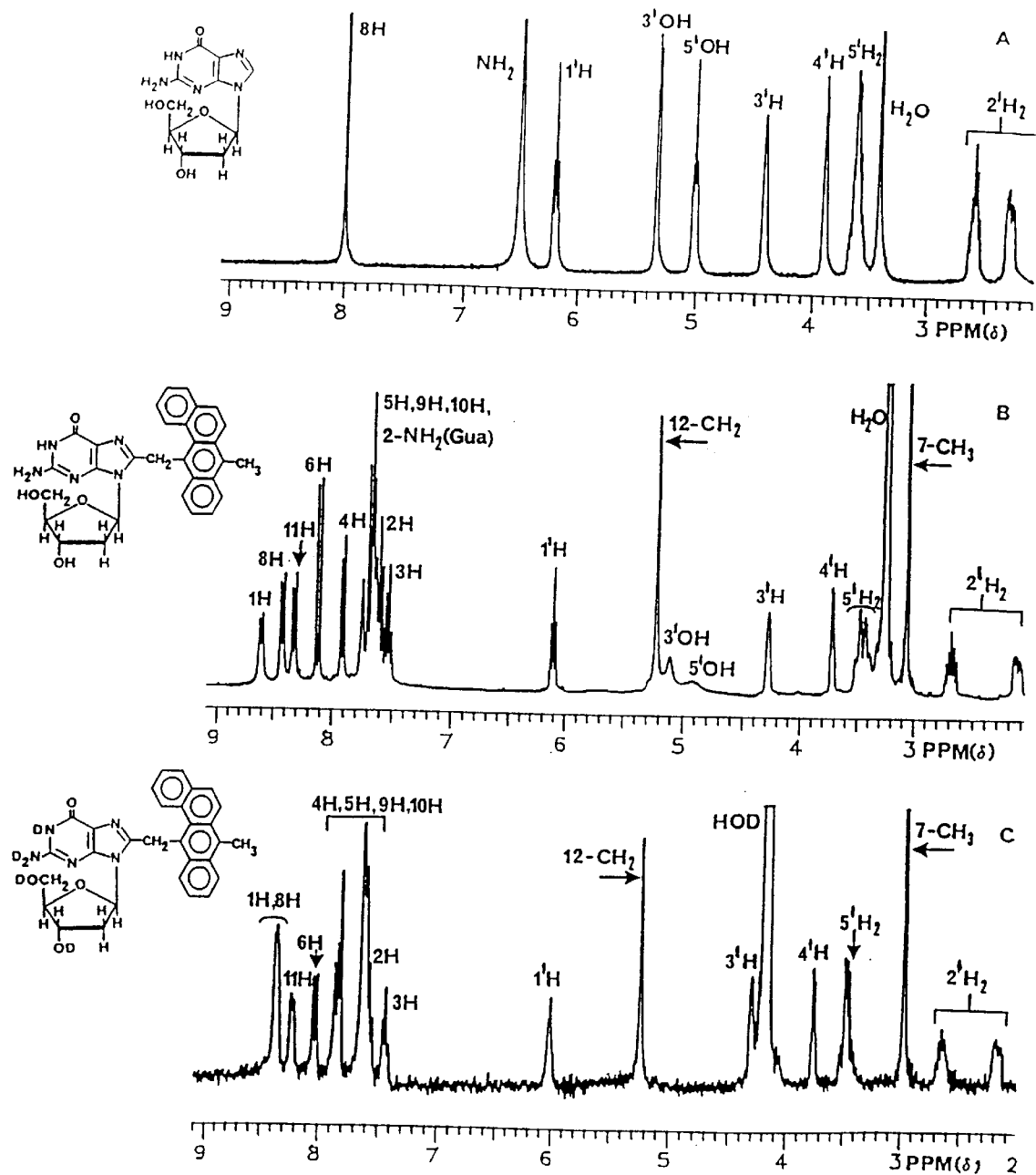
FIG. 5. NMR spectra of A) deoxyguanosine, B) 7-MBA-12-$CH_2$-C8dG, and C) 7-MBA-12-$CH_2$-C8dG after exchange with $D_2O$.
Figure 6:
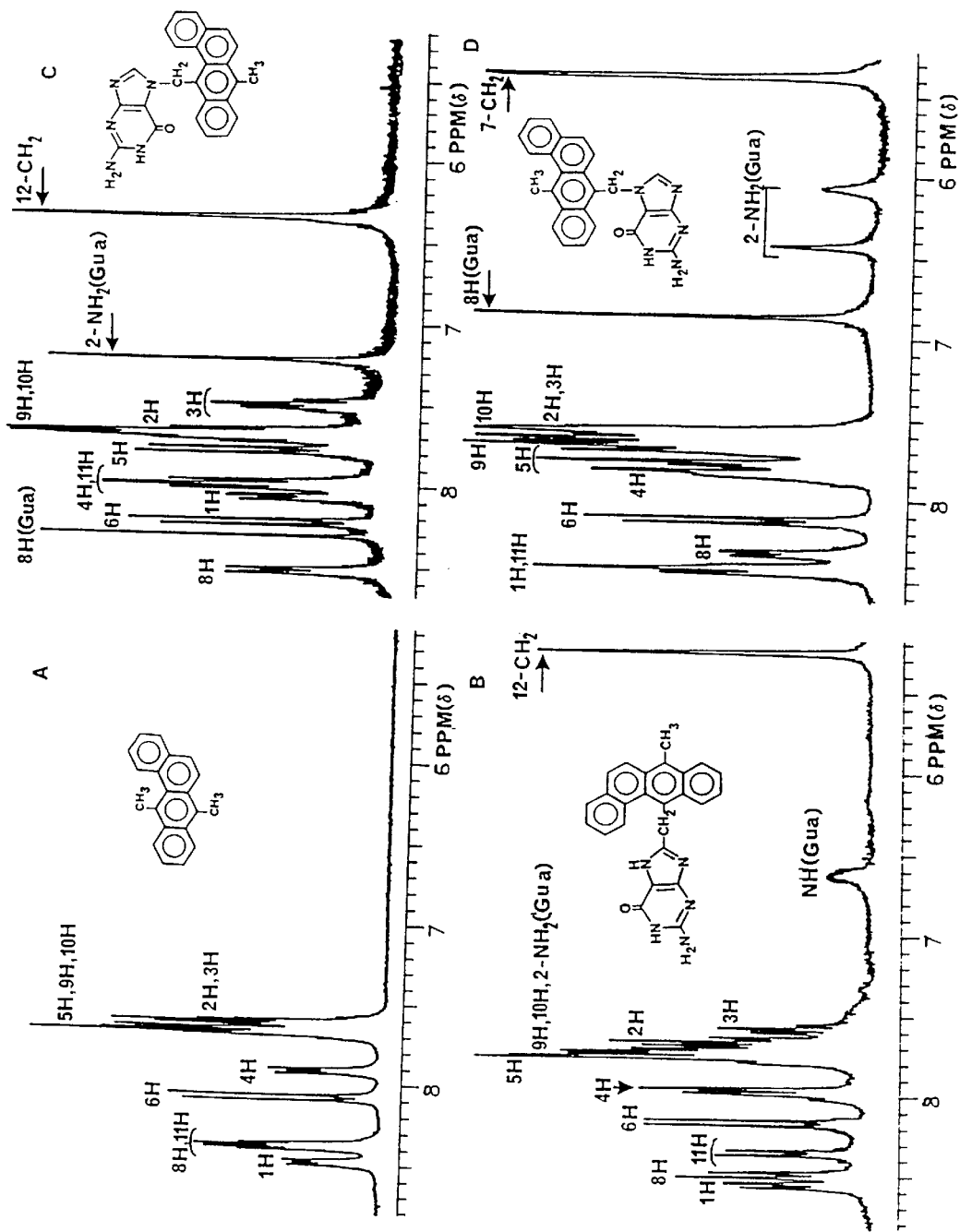
FIG. 6. NMR spectra of A) DMBA, B) 7-MBA-12-$CH_2$-C8Gua, C) 7-MBA-12-$CH_2$-N7Gua, and D) 12-MBA-7-$CH_2$-N7Gua.

The NMR spectrum of deoxyguanosine (FIG. 5A), 7-MBA-12-CH$_2$-C8dG (FIG. 5B) and the spectrum after D$_2$O exchange (FIG. 5C) are consistent with the assigned structures. The absence of the sharp singlet at 8.0 ppm assigned to the C-8 proton of the guanine moiety indicated that substitution occurred at this position in deoxyguanosine. The protons 1'-H, 2'-H, 3'-H, 4'-H and 5'-H$_2$ in the aliphatic region were unequivocally assigned by COSY. The two broad signals at 4.90 and 5.09 ppm were tentatively assigned as originating from the 5$^1$-OH and 3'-OH, respectively. These two signals totally disappeared with D$_2$O exchange (FIG. 5C), substantiating the assignment of these protons. The aromatic proton resonances, except for 8-H and 11-H, were assigned by using COSY and by comparing their chemical shifts with those of the parent DMBA (FIG. 6A). The singlet at 3.05 ppm was initially assigned to the 7-CH$_3$ and the singlet at 5.19 ppm to the 12-CH$_2$.

In the NOE experiment, irradiation of the resonance at 5.19 ppm enhanced the two doublets at 8.59 and 8.29 ppm. similarly, irradiation of the singlet resonance at 3.05 ppm enhanced the two doublets at 8.41 and 8.09 ppm. Because the two doublets at 8.59 and 8.09 ppm were already established as resonances for 1-H and 6-H, the NOE experiments allowed the 8-H and 11-H resonances to be assigned, respectively, at 8.41 and 8.29 ppm. Furthermore, the covalent bond-between deoxyguanosine and the 12-CH$_3$ group of DMBA was unequivocally established. The resonances of the NH$_2$ of guanine were thought to be part of the aromatic multiplet at 7.59–7.75 ppm (FIG. 5B). This hypothesis was supported by the integration values in the spectrum in FIG. 5B, as compared to that obtained after D$_2$O exchange (FIG. 5C). The downfield shift of the NH$_2$ of the guanine moiety was presumed to be due to its interaction with the angular ring of the DMBA moiety in the region corresponding to 2-H and 3-H, whose resonances were shifted downfield with respect to those of DMBA (FIG. 6A).

7-MBA-12-CH$_2$-C8Gua: Structure, Ultraviolet and NMR spectra

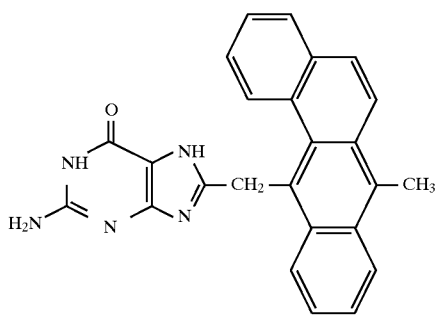

UV, absorbance wavelength maximum (nanometers), 224, 274, 294, 304, 374, 384;

NMR, 3.08 (s, 3H, 7-CH$_3$), 5.21 (s, 2H, 12-CH$_2$), 6.73 (bs, 1H, 7- or 9-NH[Gua], 7.56 (t, 1H, 3-H), 7.61 (t, 1H, 2-H), 7.65–7.80 (m, 5H, 5-H, 9-H, 10-H, 2-NH$_2$[Gua]) , 7.95 (d, 1H, 4-H), 8.14 (d, 1H, 6-H) , 8.30 (d, 1H, 11-H), 8.46 (d, 1H, 8-H), 8.53 (d, 1H, 1-H).

The NMR spectrum of 7-MBA-12-CH$_2$-C8Gua (FIG. 6B) resembles that of 7-MBA-12-CH$_2$-C8dG, except for the absence of the proton signals from the deoxyribose moiety. Assignment of protons was obtained by comparison of the chemical shifts with those of the parent compound, DMBA, and by COSY. The bond between DMBA and guanine was definitively established by NOE experiments in which the protons at 3.14 ppm, corresponding to 7-CH$_3$, and 5.21 ppm, corresponding to 12-CH$_2$, were irradiated. The broad singlet at 6.73 ppm was assigned as due to the 7- or 9-NH of guanine, as determined by their disappearance after exchange with D$_2$O. The NH$_2$ protons of guanine were deshielded in the region of the aromatic protons at 7.59–7.80 ppm, as seen for 7-MBA-12-CH$_2$-C8dG in FIG. 5B. The D$_2$O exchange and integration data supported this assignment.

7-MBA-12-CH$_2$-N7Gua: Structure, Ultraviolet and NMR spectra

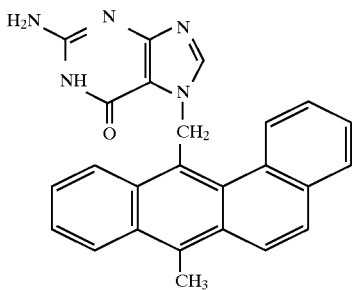

UV, absorbance wavelength maximum (nanometers), 228, 276, 296, 306, 372, 384;

NMR, 3.14 (s, 3H, 7-CH$_3$), 6.32 (s, 2H, 12-CH$_2$), 7.20 (bs, 2H, 2-NH$_2$[Gua]), 7.48 (t, 1H, 3-H), 7.61–7.72 (m, 3H, 9-H, 10-H, 2-H), 7.76 (d, 1H, 5-H), 7.91–8.04 (m, 3H, 11-H, 4-H, 1-H), 8.20 (d, 1H, 6-H), 8.26 (s, 1H, 8-H[Gua]), 8.49 (d, 1H, 8-H).

The-NMR spectrum of 7-MBA-12-CH$_2$-N7Gua (FIG. 6C) contains a sharp singlet at 8.26 ppm of the C-8 proton of guanine, indicating that this position is not substituted. In addition, the signal at 6.53 ppm, corresponding to the two protons of the NH$_2$ of guanine, is evidence that no substitution occurs at the amino group. Furthermore, this molecule does not contain the deoxyribose moiety because the corresponding proton resonances in the aliphatic region are absent. This is consistent with substitution of deoxyguanosine at N-7, which destabilizes the glycosidic bond.

The covalent bond of the DMBA moiety at the 12-CH$_2$ was assigned from NOE experiments. This was further substantiated by the shift upfield of the resonances for 1-H and 11-H, appearing at 7.91–8.04 ppm. The remaining protons of DMBA were assigned by comparing their chemical shifts with those of the parent compound, DMBA, and by using COSY.

12-MBA-7-CH$_2$-N7Gua: Structure, Ultraviolet and NMR spectra

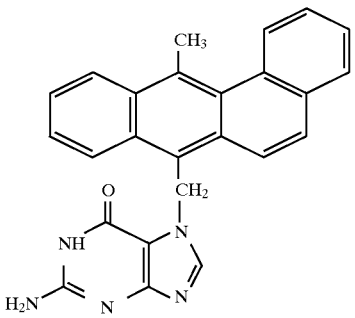

UV absorbance wavelength maximum (nanometers), 228, 274, 294, 304, 372, 384;

NMR, 3.20 (s, 3H, 12-CH$_3$) , 5.36 (s, 2H, 7-CH$_2$) , 6.09 (bs, 1H, 2-NH$_2$[Gua]), 6.41 (s, 1H, 2-NH$_2$[Gua]), 6.85 (s, 1H, 8-H[Gua]), 7.51–7.71 (m, 4H, 2-H, 3-H, 9-H, 10-H), 7.73–7.85 (m, 2H, 4-H, 5-H), 8.11 (d, 1H, 6-H), 8.31 (d, 1H, 8-H), 8.41 (m, 2H, 1-H, 11-H). The NMR spectrum is shown in FIG. 6D.

The bonding site for 12-MBA-7-CH$_2$-N7Gua was assigned from the NOE difference spectrum after irradiation of the singlet at 5.36 ppm. The irradiation resulted in enhancement of the two doublets at 8.11 and 8.31 ppm (FIG. 6D). The doublet at 8.11 ppm was established for the 6-H. Hence, the other doublet involved in the NOE experiment was assigned to 8-H, establishing that this compound is a 7-CH$_2$-Gua adduct. Other aromatic signal assignments were easily made by using COSY and by comparing with the NMR of the parent compound, DMBA. The broad singlets at 6.41 and 6.09 ppm disappeared on D$_2$O exchange. Thus, these two were assigned to the 2-NH$_2$ of guanine. The sharp singlet at 6.85 ppm was tentatively assigned as arising from the 8-H of guanine. This was consistent with substitution of the guanine moiety at N-7 by the 7-CH$_2$ of DMBA. The strong shielding effects of the 8-H of guanine and one of the NH$_2$ protons were attributed to electronic perturbation of the aromatic rings of DMBA.

7-MBA-12-CH$_2$-N7Ade: Structure, Ultraviolet and NMR spectra

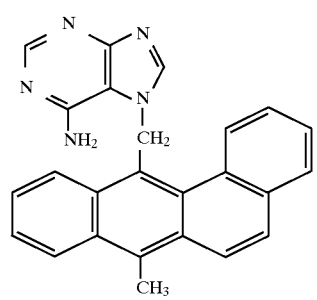

UV, absorbance wavelength maximum (nanometers), 216, 286, 294, 362, 400;

NMR, 3.17 (s, 3H, 7-CH$_3$), 6.4 (s, 2H, 12-CH$_2$), 7.16 (bs, 2H, 6-NH$_2$[Ade]), 7.42 (t, 1H, 3-H), 7.59–7.72 (m, 4H, 2-H, 8-H[Ade], 9-H, 10-H), 7.74–7.88 (m, 2H, 1-H, 5-H), 7.96–8.05 (m, 2H, 4-H, 11-H), 8.23 (d, 1H, 6-H), 8.29 (s, 1H, 2-H[Ade]), 8.54 (d, 1H, 8-H).

This molecule does not have the deoxyribose moiety, because the corresponding proton resonances in the NMR spectrum (FIG. 7A) are absent. The broad singlet at 7.16 ppm, which disappears after D$_2$O exchange, was established as the resonances of the two protons of NH$_2$ of adenine, demonstrating that no substitution occurs at the amino group. The COSY spectrum allowed all of the protons to be assigned, except for those giving the two doublets at 7.80 and 8.50 ppm, and that proton yielding the multiplet at 8.00 ppm. The sharp singlet at 8.29 ppm was designated as arising from 2-H of adenine by comparing its chemical shift with that of the corresponding proton in deoxyadenosine (spectrum not shown). The other sharp singlet, at 7.70 ppm, was tentatively assigned to the 8-H of adenine. This proton resonance is at 8.2 ppm in deoxyadenosine. Thus, the shift upfield suggested that the PAH was linked to adenine at the N-7; a similar shift was observed in FIG. 6D for 12-MBA-7-CH$_2$-N7Gua. The singlet at 3.17 ppm was initially assigned to 7-CH$_3$ and the singlet at 6.46 ppm to 12-CH$_2$.

Figure 7:
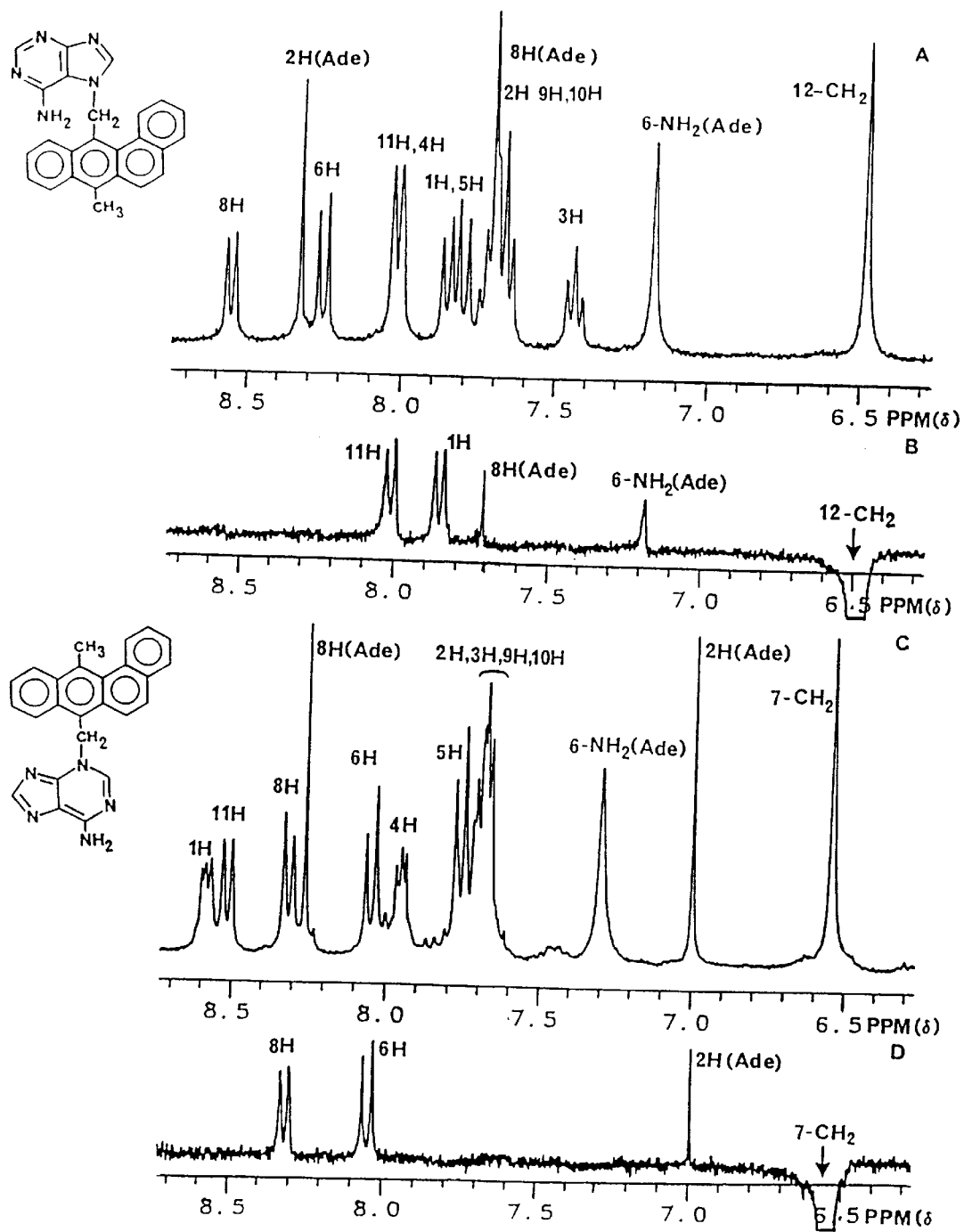
FIG. 7. A) NMR spectrum of 7-MBA-12-$CH_2$-N7Ade, B) Nuclear Overhauser Effect (NOE) spectrum of 7-MBA-12-$CH_2$-N7Ade after irradiation at 6.46 parts per million (ppm) (corresponding to 12-$CH_2$), C) NMR spectrum of 12-MBA-7-$CH_2$-N3Ade, and D) NOE spectrum of 12-MBA-7-$CH_2$-N3Ade after irradiation at 6.52 ppm (corresponding to 7-$CH_2$).

To confirm many of the assignments postulated above, NOE experiments were conducted by irradiating the two singlet resonances corresponding to 12-CH$_2$ and 7-CH$_3$ at 6.46 and 3.17 ppm, respectively. In the NOE experiment, irradiation of the singlet resonance at 3.17 ppm enhanced the intensity of the two doublets at 8.23 and 8.54 ppm. Because the doublet at 8.23 ppm was already assigned by COSY to 6-H, the other doublet was assigned to 8-H, and the singlet at 3.17 ppm was confirmed to be due to 7-CH$_3$. When the singlet resonance at 6.46 ppm was irradiated, an NOE was observed in which the doublets at 7.80 and 8.00 ppm, the sharp singlet at 7.70 ppm and the broad singlet at 7.16 ppm were enhanced (FIG. 7B). This was expected when the 12-CH$_2$ was covalently bound to N-7 of adenine, because the protons 1-H and 11-H of DMBA and the 6-NH2 and 8-H of adenine are in the vicinity of the 12-CH$_2$ of DMBA. Thus, the NOE experiment unequivocally established the bond between the N-7 of adenine and the 12-CH$_2$ of DMBA.

12-MBA-7-CH$_2$-N3Ade: Structure, Ultraviolet and NMR spectra

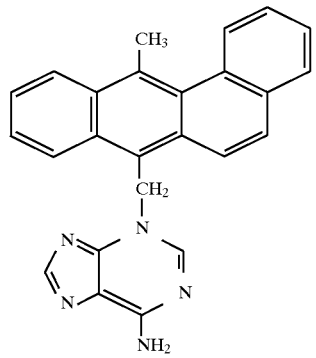

UV, absorbance wavelength maximum (nanometers), 220, 286, 294, 362, 384;

NMR, 3.39 (s, 3H, 12-CH$_3$). 6.52 (s, 2H, 7-CH$_2$), 6.98 (s, 1H, 2-H[Ade]), 7.27 (bs, 2H, 6-NH$_2$[Ade]), 7.58–7.78 (m, 5H, 2-H, 3-H, 5-H, 9-H, 10-H), 7.93 (m, 1H, 4-H), 8.02 (d, 1H, 6-H), 8.24 (s, 1H, 8-H[Ade]), 8.29 (d, 1H, 8-H), 8.48 (d, 1H, 11-H), 8.56 (m, 1H, 1-H).

The NMR spectrum (FIG. 7C) clearly showed the absence of deoxyribose. The presence of the two prominent singlets at 6.98 and 8.24 ppm, initially assigned as the resonances of 2-H and 8-H of adenine, indicated that these positions were not substituted. In addition, the two protons that give a resonance at 7.27 ppm were established as the 6-NH$_2$ of adenine, demonstrating that no substitution occurred at the amino group. The chemical shifts and proton multiplicities of this spectrum did not correspond to those of the NMR of the N7-Ade adduct (FIG. 7A), demonstrating that this was not an N-7 adduct. Because N-3 is a nucleophilic group of adenine and a covalent bond to this position would destabilize the glycosidic bond of deoxyribose, it was logical to hypothesize that adduction occurred at N-3. This was further substantiated by the large upfield shift, 1.3 ppm, of the 2-H proton resonance.

Once again NOE experiments unequivocally proved the structure af the adduct. The NOE spectrum (FIG. 7D) obtained from irradiating the singlet resonance at 6.52 ppm showed enhancement of the 6-H and 8-H doublets at 8.02 and 8.29 ppm, respectively, and the sharp singlet at 6.98 ppm, corresponding to the 2-H of adenine (FIG. 7D). The enhancement of the two doublets unequivocally indicated that the 7-CH$_2$ of DMBA was the position of linkage in the adduct, and the singlet at 3.39 ppm corresponded to a resonance for the 12-CH$_3$. The enhancement of the signal of the 2-H of adenine was proof that the N-3 of adenine was bound to DMBA. On the other hand, the absence of enhancement of the NH$_2$ signal in the NOE experiment clearly established that this adduct did not involve binding at N-7 of adenine; this was in contrast to the enhancement observed in FIG. 7B for the N7-Ade adduct. The remaining protons in the aromatic region were designated by comparing their chemical shifts with those of the parent compound, DMBA and by employing COSY.

The following two examples demonstrate the preparation of two new adducts by chemical reaction in the diol epoxide pathway of metabolic activation of BP. In EXAMPLE 5, formation of a novel adduct between BPDE and deoxyguanosine is demonstrated, and, in EXAMPLE 6, formation of a novel adduct between BPDE and deoxyadenosine is demonstrated. Many other laboratories have worked for over a decade without success to synthesize these adducts.

EXAMPLE 5

Adduct Produced in the Reaction of BPDE and Deoxyguanosine

In contrast to prior methodology, adducts between BPDE and deoxyguanosine were formed by using the novel procedure of the present invention, which is as follows: a mixture of 5 mg (0.016 mmol) of BPDE and 50 mg (0.187 mmol) of deoxyguanosine were dissolved in 5 mL of dry DMF and stirred at 100° C. for 2 hours under a stream of dry argon. The unique combination of dry DMF solvent and stirring at high temperature for 2 hours was absolutely essential for the reaction to succeed.

After cooling the solution to room temperature, an equal amount of dimethylsulfoxide (DMSO; 5 mL) was added, and the solution was filtered through a DMSO-resistant 0.45 micrometer filter. Analysis of an aliquot by HPLC by eluting with 20% CH$_3$CN in H$_2$O for 5 minutes, followed by a linear gradient to 100% CH$_3$CN in 80 minutes showed the complete disappearance of BPDE and the presence of two products.

The two products were purified by preparative HPLC in CH$_3$CH/H$_2$O (gradient as above with a flow rate of 6-mL per minute), followed by CH$_3$OH/H$_2$O gradient (as described for BP and deoxyguanosine adducts with a flow rate of 6 mL per minute). Their structures were established by NMR and FAB MS. One product was BP tetraol and the other was the BPDE-DNA adduct, identified as BPDE-10-N7Gua (64% yield). This adduct was used to demonstrate for the first time that it is not formed biologically in detectable amounts; this was an unexpected finding.

BPDE-10-N7Gua: Structure, Ultraviolet and NMR spectra

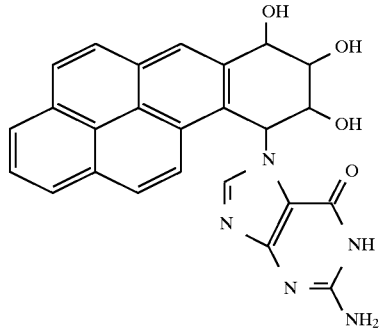

Figure 8:
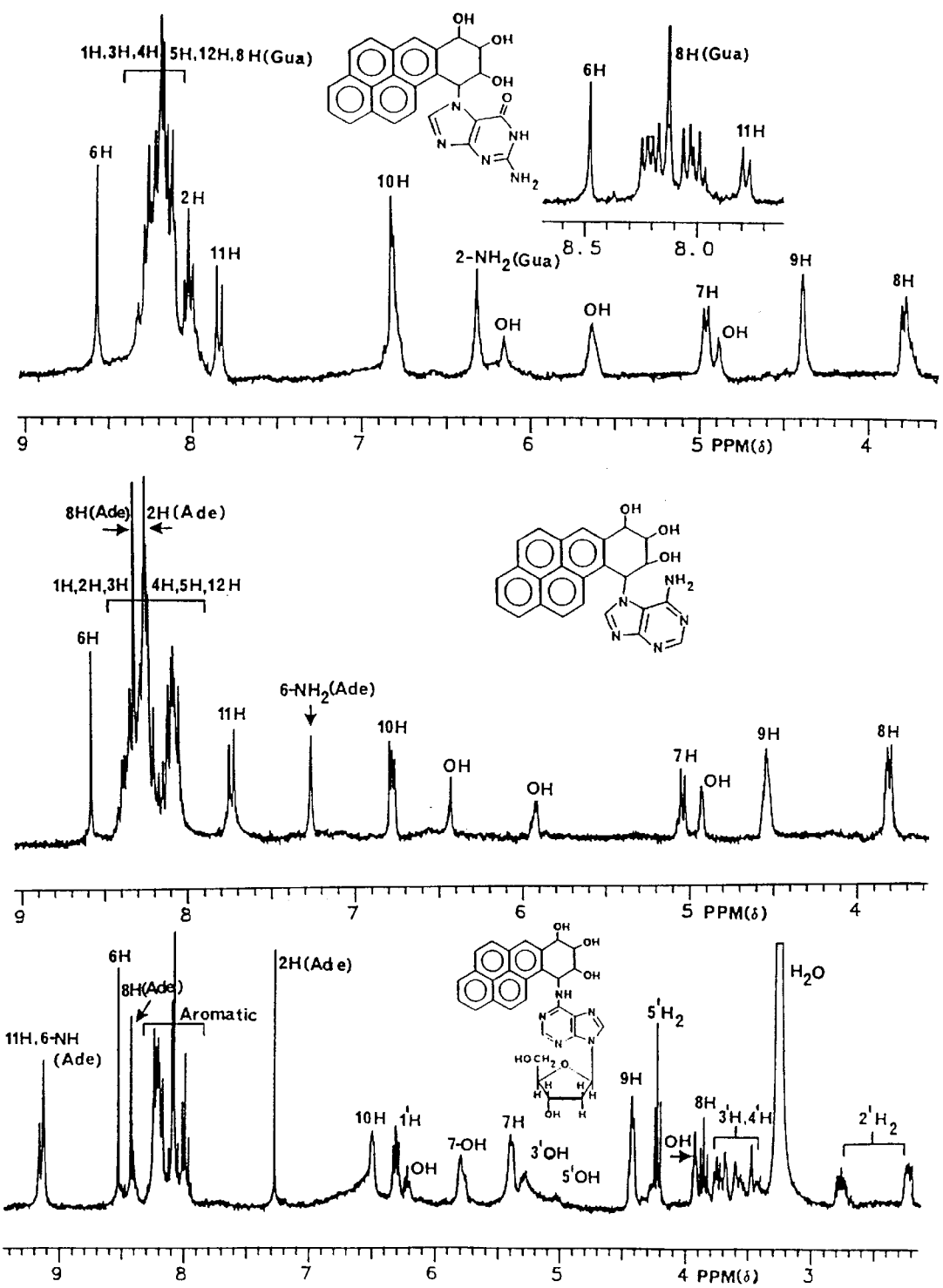
FIG. 8. NMR spectra of a) BPDE-10-N7Gua, b) BPDE-10-N7Ade, and c) BPDE-10-$N^6$dA.

UV, absorbance wavelength maximum (in nanometers) 246, 278, 330, 346;

NMR, 3.76, (dd, 1H, 8-H, J=8.6 Hz), 4.08–4.23 (m, 1H, OH), 4.36 (bs, 1H, 9-H), 4.86 (bs, 1H, OH), 4.95 (d, 1H, 7-H, $J_{7,8}$=8.6 Hz), 5.63 (bs, 1H, OH), 6.30 (bs, 2H, 2-$NH_2$ [Gua]), 6.80 (d, 1H, 10-H, J=5.7 Hz), 7.83 (d, 1H, 11-H, J=9.2 Hz), 7.99 (t, 1H, 2-H), 8.06–8.33 (m, 6H, 1-H, 3-H, 4-H, 5-H, 12-H, 8-H[Gua]), 8.57 (s, 1H, 6-H). The spectrum for this adduct is shown in FIG. 8A.

EXAMPLE 6

Adducts Produced by Reaction of BPDE and Deoxyadenosine

The reaction conditions described in detail in EXAMPLE 5 were also used with BPDE and deoxyadenosine. Analysis of an aliquot by HPLC in $CH_3CN/H_2O$ showed the disappearance of BPDE and the presence of four products, three of which were DNA adducts. These were purified by preparative HPLC and identified as BP tetraol (10%), and the following three adducts: BPDE-10-N7Ade (36%), and two isomers of BPDE-10-$N^6$dA (first eluting, 25%, and second eluting 28%). The BPDE-10-N7Ade was used to demonstrate for the first time that it was formed biologically. The complete chemical name for this latter adduct is: 10-(adenin-7-yl)-7,8,9-trihydroxy-7,8,9,10- tetrahydrobenzo[a]pyrene. The structure, UV and NMR spectra of this latter compound follow.

BPDE-10-N7Ade: Structure, Ultraviolet and NMR spectra

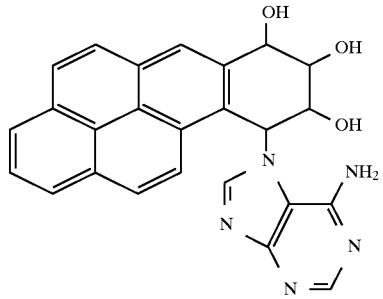

UV, absorbance wavelength maximum (in nanometers): 246, 279, 318, 331, 346;

NMR 3.78 (dd, 1H, 8-H), 4.52 (dd, 1H, 9-H), 4.91 (bs, 1H, —OH), 5.01 (d, 1H, 7-H, J=7.0 Hz), 5.90 (bs, 1H, —OH), 6.40 (bs, 1H, —OH), 6.75 (d, 1H, 16-H), 7.05 (s, 1H, 8-H[Ade]), 7.24 (bs, 2H, 6-NH2[Ade]), 7.72 (d, 1H, aromatic, J=9.0 Hz), 7.98–8.41 (m, 7H, aromatic and 2-H [Ade]), 8.56 (s, 1H, 6-H). The NMR spectrum for this adduct is shown in FIG. 8B.

The two mixed isomeric forms of BPDE-10-$N^6$dA adducts were isolated and characterized. Their complete chemical names are:

10α-(deoxyadenosin-$N^6$-yl-7 β,8α,9β-trihydroxy-7,8,9,10-tetrahydro-benzo[a]pyrene; and 10β-(deoxyadenosin-$N^6$-yl-7β,8α,9αtrihydroxy-7,8,9,10-tetrahydrobenzo[a]pyrene.

A single structure is herein presented, since the isomers cannot yet be separated. The alpha and beta forms refer to whether the bond to the deoxyadenosine ring is above or below the plane of the benzopyrene rings.

The two BPDE-10-$N^6$dA adduct isomers: Structure, Ultraviolet and NMR spectra

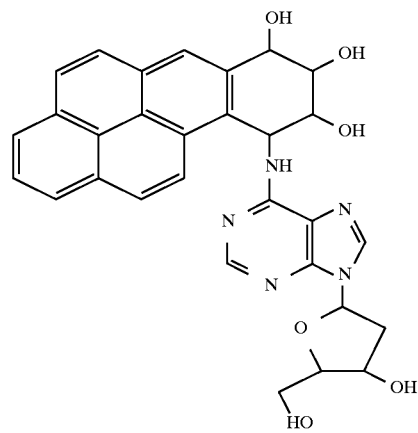

UV, absorbance wavelength maximum (in nanometers) 245, 280, 316, 331, 346;

NMR, 2.34 (m, 1H, 2'-H), 2.74 (m, 1H, 2'-H), 3.57 (m, 2H, 5'-H2), 3.68 (m, 1H, 4'-H), 3.85 (dd, 1H, 8-H), 3.90 (bs, 1H, OH), 4.19 (dd, 1H, 9-H), 4.39 (m, 1H, 3'-H), 4.98–5.52 (m, 2H, 3'-OH, 5'-OH), 5.39 (d, 1H, 7H, J=7.4 Hz), 5.78 (bs, 1H, 7-OH), 6.06 (bs, 1H, OH), 6.27 (t, 1H, 1'-H), 6.55 (d, 1H, 10-H, J=13.7 Hz), 7.26 (s, 1H, 2-H[Ade]), 7.89–8.28 (m, 6H, 1-H, 2H, 3-H, 4-H, 5-H, 12-H), 8.39 (s, 1H, 8-H[Ade]), 8.52 (s, 1H, 6-H), 9.13 (m, 2H, aromatic, J=10.2 Hz; 6NH[Ade]). The spectrum for the isomers of this adduct are shown in FIG. 8C.

Covalent binding of BP to DNA by the enzyme horseradish peroxidase yielded three depurination adducts: BP-6-N7Gua, BP-6-C8Gua, and BP-6-N7Ade in approximate ratio 1:1:5. When the binding of BP to DNA was catalyzed by cytochrome P-450, the predominant adducts were the same three depurination adducts in about the same ratio, plus a small amount of BPDE-10-N7Ade. These results demonstrated that cytochrome P-450 primarily binds BP to DNA by one-electron oxidation. Similar results were obtained when the target tissue mouse skin was treated with BP and the stable and depurination adducts were analyzed.

Covalent binding of DMBA to DNA by the enzymes horseradish peroxidase and cytochrome P-450 yielded 7-MBA-12-$CH_2$-N7Gua and 7-MBA-12-$CH_2$-N7Ade, whereas 12-MBA-7-$CH_2$-N7Gua was not formed. Thus, these two adducts were obtained via a benzylic radical intermediate, forging a link between the electrochemical and enzymatic experiments. These results also demonstrated that cytochrome P-450 binds DMBA to DNA by one-electron oxidation. Similar results were obtained when the target tissue mouse skin was treated with DMBA and the stable and depurinationr adducts were analyzed. Furthermore, the 12-CH$_3$ group was critical in the binding of the DMBA to the nucleophiles of DNA. The role of the 12-CH$_3$ group was also indicated by carcinogenicity results.

The identification of biologically-formed PAH-DNA adducts was impossible without the use of synthesized authentic adducts. The synthetic procedures described in the present invention have led to the recognition of new adducts which are formed biologically, thereby radically changing the understanding of PAH adduction.

In summary, the radical cation of DMBA reacts with deoxyguanosine to produce the novel adducts 7-MBA-12-CH$_2$-C8dG, 7-MBA-12-CH$_2$-N7Gua and 12-MBA-7-CH$_2$-N7Gua. The 7-MBA-12-CH$_2$-C8Gua was a secondary product arising from electrochemical oxidation of the corresponding C8-dG adduct. With deoxyadenosine, the two adducts which formed, in approximately equal amounts, were 7-MBA-12-CH$_2$-N7Ade and 12-MBA-7-CH$_2$-N3Ade: The synthesis was not only a demonstration of the reactivity of nucleosides and DMBA under oxidizing conditions, but also a source for necessary reference materials for studying the DMBA-DNA adducts formed in biological systems.

The radical cation of BP reacted with deoxyguanosine to produce BP-6-N7Gua, BP-6-C8Gua, BP-6-C8dG, and the novel adducts BP-6-N3dG and BP-6-N$^2$dG. With deoxyadenosine, the only adduct formed was BP-6-N7Ade.

BPDE reacted with deoxyguanosine to produce BPDE-10-N7Gua, whereas it reacted with deoxyadenosine to yield BPDE-10-N7Ade and two isomers of BPDE-10-N$^6$dA.

EXAMPLE 7

Heterocyclic Aromatic Hydrocarbon-DNA Adducts Synthesis of 7-H-dibenzo[e,g]carbazole (DBC)-DNA-Adducts The relatively low oxidation potential and the charge localization of the DBC radical cation led to the hypothesis that this compound can be metabolically activated by one-electron oxidation. Iodine oxidation in the presence of deoxyguanosine produced three adducts: DBC-5-N7-guanine; DBC-6-N7guanine; and DBC-6-C8-guanine. In the presence of adenine, four adducts were formed: DBC-5-N7-adenine; DBC-5-N3-adenine; DBC-6-N3-adenine and DBC-5-N1adenine.

Formation of these adducts indicates that DBC radical cation has charge localized at C-5 and C-6. Activation of DBC by horse radish peroxidase in the presence of DNA afforded the depurinating adducts in the following yields: DBC-5-N7-guanine (19%); DBC-6-N7-guanine (13%); DBC-5-N7-adenine (27%); and DBC-5-N3-adenine (9%). The remainder (32%) was unidentified adducts found stable in DNA. The adducts formed after activation in rat liver microsomes were as follows: DBC-5-N7-guanine (11%); DBC-6-N7-guanine (32%); DBC-5-N7-adenine (53%) and 4% unidentified stable adducts. These results show that activation of DBC by horse radish peroxidase or cytochrome P-450 predominantly produces depurinating adducts formed by one-electron oxidation. These adducts generate apurinic sites in DNA, which, if not repaired can be mutagenic.

EXAMPLE 8

Formation of Adducts of 6-Fluorobenzo[a]pyrene and Deoxyctosine

Electrochemical one-electron oxidation of 6FBP in the presence of deoxycytosine produces the N3-cytosine adduct, which is the position of the highest charge density after C-6 in the BP. BP quinones are formed by reaction of 6-FBP and traces of moisture that can enter the system during the reaction. Thus, reaction of 6-FBP with acetate ion and water occurs at C-6 whereas it takes place regiospecifically at C-1 and C-3 with the N-3 of of cytosine. The adducts thus produced will be used as standard compounds in the determination of such depyrimidination adducts in biological systems.

The capacity to detect adducts of PAH and DNA nucleosides in urine is an important tool for monitoring human exposure to organic carcinogens such as BP in cigarette smoke and air pollutants, especially in certain-industrial settings. The level of adducts detectable in certain biological samples can be expected to be in the femtomole range. The synthesized adducts of this invention, when conjugated with an immunogenic carrier, constitute the haptenic portion thereof. These conjugates are immunogenic and are antigens for the production of highly specific antibodies useful in immunoassays for the detection of DNA-PAH adducts in the femtomole range in biological specimens.

Preparation of Immunogenic Conjugates

In one embodiment, the adduct/hapten is linked to the carrier via a rigid heterofunctional spacer moiety of about 12 angstroms (MCCCl) or a structurally less complex heterobifunctional spacer moiety of about 8 angstroms (PDPCl). This enhances recognition of the hapten by-the immune system of the antibody-producing host. When the carrier is a protein, such as keyhole limpet hemocyanin (KLH), it is also preferred to carry out the conjugation reaction in an environment, such as 20–50% DMSO in an aqueous buffer, that promotes dissolution of the hydrophobic adduct and thereby reduces sequestration of the PAH adduct in hydrophobic regions of the carrier. A conjugate complex with about 200 molecules of the adduct per molecule of carrier has been found to be an effective immunogen, particularly for the production of monoclonal antibodies (MAbs).

EXAMPLE 9

7-(Benzo[a]Pyren-6-yl)Guanine (BP-6-N7Gua) Linked to KLH via N-Maleimidomethylcyclohexane-1-carboxyl Chloride (MCCCl)

Ten to 20 mg of MCCCl is combined with BP-6-N7Gua in 1–2 mL dry pyridine in a molar ratio of 2:1. The reaction, forming an amide bond between the free amino (N$^2$) group of BP-6-N7Gua and the carboxyl chloride group of MCCCl, is allowed to proceed in vacuo for 2 hours at room temperature (22–25 degrees C.). The reaction product 7-(benzo[a]pyren-6yl)guanine-2-(N-maleimidomethyl) cyclohexane-1-carboxylate (MCC-BP-6-N7Gua), generated in high yield, is purified to 99% purity by a combination of normal phase chromatography on a silica column eluted with 90% chloroform/10% acetone, and reverse phase high performance liquid chromatography on a C-18 column eluted with a-gradient of 90% methanol/10% water to 100% methanol. The structure of the purified conjugate is verified by nuclear magnetic resonance analysis demonstrating 1) the proton of the new amide bond between the carbonyl group of MCCCl and the $N^2$ of BP-6-N7Gua, 2) the loss of the free amino protons of the $N^2$ of BP-6-N7Gua, 3) the protons of the cyclohexane ring of MCCCl, 4) the proton doublet of the methylene bridge of MCCCl, and 5) the maleimide singlet protons. The purified conjugate (MCC-BP-6-N7Gua), stored as a dry powder, is dissolved in 100% DMSO just prior to conjugation with carrier protein.

Spacer/Adduct Conjugate (MCC-BP-6-N7Gua)

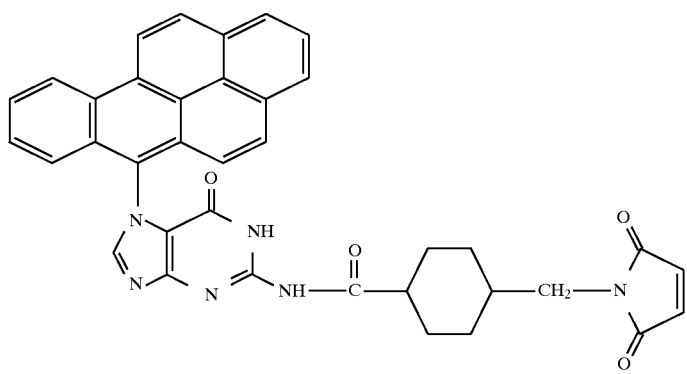

Free sulfhydryl groups are introduced into lysyl side chains of KLH the carrier protein of the immunogenic complex. Twenty mg of KLH is dissolved in 1 mL of reaction buffer consisting of a mixture of 0.10M borate, 0.10M NaCl and 0.05M ethylenediamine tetraacetate (EDTA) in water-, adjusted to pH 9.0. Traut's reagent (iminothiolane) dissolved in reaction buffer is added in a volume of 40 μL to 1 mL of KLH solution to produce a 20 molar excess of Traut's reagent versus free ε-amino groups of the lysyl residues in KLH. It is estimated that there are approximately 500 available c-amino groups per molecule of KLH (MW=1.3 ×10$^7$). The reaction between these free amino groups and Traut's reagent, converting the free amino groups into free sulfhydryl groups, is allowed to proceed in an argon atmosphere at 37 degrees C. for 2 hours. The reaction is stopped and sulfhydryl KLH (SH-KLH) separated from unreacted Traut's reagent by dialysis against phosphate buffer (0.10M sodium phosphate, 0.10M NaCl and 0.05M EDTA in water, adjusted to pH 7.2. The concentration of free protein sulfhydryls is determined with Ellman's reagent and the molar ratio of free sulfhydryl groups to KLH is computed assuming a molecular weight of 1.3×10 sup 7 Da for KLH. Under the present conditions, approximately 300–400 free sulfhydryl groups are introduced onto the surface of each molecule of KLH. Traut's modified KLH (SH-KLH) is prepared just prior to use in the coupling of MCC-BP-6-N7Gua with SH-KLH.

The linker-adduct conjugate (MCC-BP-6-N7Gua) is coupled to SH-KLH by a thioether bond between the maleimide group of MCC-BP-6-N7Gua and the free sulfhydryl groups of SH-KLH. Two mg of MCC-BP-6-N7Gua is dissolved in 200 μL of DMSO and combined with 1.0 mL of the dialyzed SH-KLH solution. The final coupling reaction mixture contains MCC-BP-6-N7Gua in a 10 molar excess versus free sulfhydryl groups of SH-KLH. The reaction mixture is incubated in an atmosphere of argon for 2 hours at 37 degrees C., then the reaction is terminated and the immunogenic complex (KLH-S-MCC-BP6-N7Gua) is separated from unreacted MCC-BP-6-N7Gua by gel sieving on a Sephadex G25 column (0.5×9 cm) equilibrated with purification buffer (0.10M sodium phosphate and 0.10M NaCl, at pH 7.5). The void volume is collected and if necessary concentrated to 10 mg protein/mL by ultrafiltration. The concentration of free protein sulfhydryls is determined with Ellman's reagent and the molar ratio of free sulfhydryl groups to SH-KLH is computed assuming a molecular weight of 1.3×10 sup 7 Da for KLH. Under the reaction conditions for coupling MCC-BP-6-N7Gua with SH-KLH, the molar ratio of free sulfhydryl groups to SH-KLH is 50–100:1. The difference between the molar ratio of free sulfhydryl groups to SH-KLH before coupling (300–400:1) and after coupling (50–100:1) with MCC-BP-6-N7Gua represents the molar ratio of MCC-BP-6-N7Gua to SH-KLH (200–350:1) in the immunogenic complex. Glycerol is added as a protein stabilizing agent to a concentration of 25% (by volume) to the solution of the immunogenic complex, and this stabilized solution is stored for up to 12 months at −20 degrees C.

EXAMPLE 10

7-(Benzo[a]Pyren-6-yl)Guanine (BP-6-N7Gua) Linked to KLH via3-(2-pyridyldithio)propionyl Chloride (PDPCl)

Procedures for the preparation of an immunogenic complex consisting of a plurality of BP-6N7Gua adducts linked to KLH via 3-(2pyridyldithio)propionyl chloride (PDPC1) are directly analogous to those procedures for the preparation of an immunogenic complex consisting of a plurality of BP-6-N7Gua adducts linked to KLH via N-Maleimidomethyl-cyclo-hexane-1-carboxyl Chloride (MCCCl) (EXAMPLE 7).

Spacer/Adduct conjugate (PDP-BP-6-N7Gua)

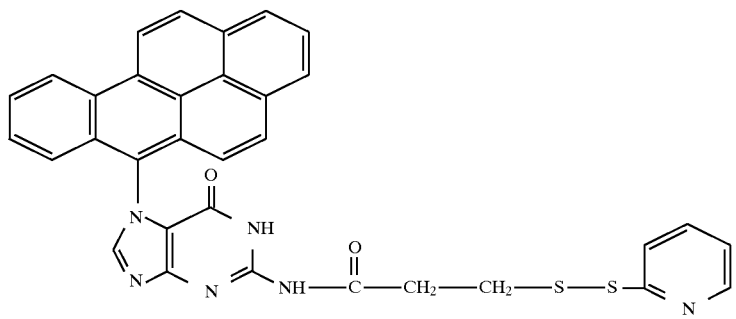

Preparation of Adduct-Specific Antibody Capture Complexes

In one embodiment the adduct/hapten is linked to the adhesion molecule (generally a protein) via a rigid heterobifunctional spacer moiety of about 12 angstroms (MCCCl) or a structurally less complex heterobifunctional spacer moiety of about 5 angstroms (PDPCl). This enhances recognition of the hapten by hapten-specific antibodies. When the adhesion molecule is a protein, such as bovine serum albumin (BSA), it is also preferred to carry out the coupling reaction in an environment, such as 20–50% DMSO in an aqueous buffer, that promotes dissolution of the hydrophobic adduct and thereby reduces sequestration of the PAH adduct in hydrophobic regions of the protein. A conjugate complex with between about 5 and about 15 molecules of adduct/hapten per molecule of BSA has been found to be an effective capture complex in both a screening ELISA for detection of adduct-specific monoclonal antibodies and in a competitive ELISA for detection of free adduct/hapten.

EXAMPLE 11

7-(Benzo[a]Pyren-6-yl)Guanine (BP-6-N7Gua) Linked to BSA via N-Maleimidomethylcyclohexane-1-carboxyl Chloride (MCCCl)

Ten to 20 mg of MCCCl is combined with BP-6N7Gua in 1–2 mL dry pyrdine in a molar ratio of 2:1. The reaction, forming an amide bond between the free amino ($N^2$) group of BP-6-N7Gua and the carboxyl chloride group of MCCCl, is allowed to proceed in vacuo for 2 hours at room temperature (22–25 degrees C.). The reaction product 7-(benzo [a]pyren-6yl)guanine-2-(N-maleimidomethyl) cyclohexane-1-carboxylate (MCC-BP-6-N7Gua), generated in high yield, is purified to 99% purity by a combination of normal phase chromatography on a silica column eluted with 90% chloroform/10% acetone, and reverse phase high performance liquid chromatography on a C-18 column eluted with a gradient of 90% methanol/10% water to 100% methanol. The structure of the purified conjugate is verified by nuclear magnetic resonance analysis demonstrating 1) the proton of the new amide bond between the carbonyl group of MCCCl and the $N^2$ of BP-6-N7Gua, 2) the loss of the free amino protons of the $N^2$ of BP-6-N7Gua, 3) the protons of the cyclohexane ring of MCCCl, 4) the proton doublet of the methylene bridge of MCCCl, and 5) the maleimide singlet protons. The purified conjugate (MCC-BP-6-N7Gua), stored as a dry powder, is dissolved in 100% DMSO just prior to conjugation with the adhesion molecule (protein).

Free sulfhydryl groups are introduced into lysyl side chains of bovine serum albumin (BSA) the adhesion moleeule.of the capture complex. Twenty mg of BSA is dissolved in 1 mL-of reaction buffer consisting of a mixture of 0.10M borate, 0.10M NaCl and 0.05M ethylenediamine tetraacetate (EDTA) in water, adjusted to pH 9.0. Traut's reagent (iminothiolane) dissolved in reaction buffer is added in a volume of 20 μL to 1 mL of BSA solution to produce a 20 molar excess of Traut's reagent versus free ϵ-amino groups of the lysyl residues in BSA. It is estimated that there are between about 30 and 35 available c-amino groups per molecule of BSA (MW=$6.7\times10^4$). The reaction between these free amino groups and Traut's reagent, converting the free amino groups into free sulfhydryl groups, is allowed to proceed in an argon atmosphere at 37 degrees C. for 2 hours. Sulfhydryl BSA (SH-BSA) separated from unreacted Traut's reagent by dialysis against a buffer consisting of a mixture of 0.10M sodium phosphate, 0.10M NaCl and 0.05M EDTA in water, adjusted to pH 7.2. The concentration of free protein sulfhydryls is determined with Ellman's reagent and the molar ratio of free sulfhydryl groups to BSA is computed assuming a molecular weight of $6.7\times10^4$ Da for BSA. Under the present conditions, approximately 20–30 free sulfhydryl groups are introduced on to the surface of each molecule of BSA. Traut's modified BSA (SH-BSA) is prepared just prior to use in the coupling of MCCBP-6-N7Gua with SH-BSA.

The linker-adduct conjugate (MCC-BP-6-N7Gua) is coupled to SH-BSA by a thioether bond between the maleimide group of MCC-BP-6-N7Gua and the free sulfhydryl groups of SH-BSA. Two mg of MCC-BP-6-N7Gua is dissolved in 200 μL of DMSO and combined with 1.0 mL of the dialyzed SH-BSA solution. The final coupling reaction mixture contains MCC-BP-6-N7Gua in a 10 molar excess versus free sulfhydryl groups of SHBSA. The reaction mixture is incubated in an atmosphere of argon for 2 hours at 37 degrees C. The reaction is terminated and the capture complex (BSA-S-MCC-BP-6-N7Gua) is separated from unreacted MCC-BP-6N7Gua by gel sieving on a Sephadex G25 column (0.5×9 cm) equilibrated with purification buffer (0.10M sodium phosphate and 0.10M NaCl, at pH 7.5). The void volume is collected and if necessary concentrated to 10 mg protein/mL by ultrafiltration. The concentration of free protein sulfhydryls is determined with Ellman's reagent and the molar ratio of free sulfhydryl groups to SH-BSA is computed assuming a molecular weight of $6.7\times10^4$ Da for BSA. Under the reaction conditions for coupling MCC-BP-6N7Gua with SH-BSA, the molar ratio of free sulfhydryl groups to SH-BSA is 10–15:1. The difference between the molar ratio of free sulfhydryl groups to SH-BSA before coupling (20–25:1) and after coupling (10–15:1) with MCC-BP-6-N7Gua represents the molar ratio of MCCBP-6-N7Gua to SH-BSA (-5–15:1) in the capture complex. Glycerol is added as a protein stabilizing agent to a concentration of 25% (by volume) to the solution of the capture complex, and this stabilized solution is stored for up to 12 months at −20 degrees C.

EXAMPLE 12

7-(Benzor[a]Pyren-6-yl)Guanine (BP-6-N7Gua) Linked to BSA via 3-(2-pyridvldithio)propionyl Chloride (PDPC1)

Procedures for the preparation of a capture complex consisting of a plurality of BP-6-N7Gua adducts linked to BSA via 3-(2-pyridyldithio)propionyl chloride (PDPCl) are directly analogous to those procedures for the preparation of a capture complex consisting of a plurality of BP-6-N7Gua adducts linked to BSA via N-Maleimidomethylcyclohexane-1-carboxyl Chloride (MCCCl).

Preparation of Antibodies

The following example demonstrates the use of a PAH-DNA conjugate (immunogenic complex) of this invention in the preparation of monoclonal antibodies.

EXAMPLE 13

Monoclonal Antibodies Specific for 7-(Benzo[a]pyren-6-yl)Guanine

Monoclonal antibodies to a depurination adduct (BP-6-N7Gua) of this invention are prepared with lymphocytes collected from BALB/c mice immunized with an immunogenic complex of this invention. An immunization mixture is prepared by emulsifying a glycerol-stabilized solution of immunogenic complex (4 mg KLH-MCC-BP-6-N7Gua/mL) and an equal volume of Freund's complete adjuvant. Five to eight BALB/c mice (males) 8–12 weeks of age are given a single subcutaneous injection of 20–30 microliters of the immunization mixture (40–60 micrograms of KLH-MCC-BP6-N7Gua) into each hind foot. Two weeks later, the enlarged popliteal lymph nodes are surgically removed under sterile conditions and disrupted to a single-cell suspension in complete medium (RPMI 1640 medium supplemented with L-glutamine and 10% fetal bovine serum and containing gentamicin (50 ug/mL). The cells are washed two times by centrifugation, then suspended in complete medium. Three-day cultures of mouse myeloma cells (P3X63-Ag.653) are harvested and the cells are washed one time by centrifugation, then suspended in complete medium. The viabilities of the cell suspensions are determined and the suspensions are combined in a ratio of 10:1 i.e. viable lymph node cells to viable myeloma cells. After the cells are mixed and pelleted and all of the medium is removed, they are fused by-incubation for one minute with 1 mL of a solution of 42% (by volume) polyethylene glycol 4000 and 15% (by volume) of dimethylsulfoxide in phosphate buffered saline at pH 7.2. The cell suspension is slowly diluted to 10 mL with complete medium, transferred to a 75 cm sup 2 T-flask, then incubated for 2–4 hours at 37 degrees C. The fusion products are harvested, pelleted by centrifugation, then suspended in selection medium (complete medium containing 13.6 µg hypoxanthine, 0.19 µg aminopterin, and 3.88 µg thymidine per milliliter and 10% of the B cell growth and cloning factor "Origen HCF") to a density corresponding to 4×10 sup 5 myeloma cells in the original cell fusion mixture per milliliter. The resultant suspension of fusion products is plated in microwell culture plates at a rate of 200 uL per well, then incubated at 37 degrees C. in a water-saturated atmosphere of 5% carbon dioxide and 95% air.

After 10–14 days of incubation, 50–100 µL of culture medium is collected from each microculture in which cell growth covers approximately 50% of the bottom of the microwell. These primary microcultures are replenished with 100 µL of HT medium (complete medium supplemented with 13.6 µg hypoxanthine and 3.88 µg thymidine per ml and 10% B cell growth and cloning factor). The samples of culture medium are tested for the presence of antibody reactive with capture complex (BSA-MCC-BP-6-N7Gua, a product of this invention) by a two-site labelled-antibody ELISA described below. Those primary microcultures containing antibody reactive with capture complex are transferred to 6-well culture plates where their cell numbers increase during a 4–7 day culture period.

The expanded primary cell cultures, containing antibodies reactive with capture complex (BSA-MCC-BP-6-N7Gua), are cloned by limiting dilution according to the following procedures. Each expanded culture is diluted to 9, 3, and 1 cells per 200 µL with HT medium and plated to a 96-well plate such that 32 wells are seeded with 9 cells/well, 32 wells are seeded with 3 cells/well and 32 wells are seeded with 1 cell/well. The plates are incubated at 37 degrees C. in a water-saturated atmosphere of 95% carbon dioxide and 5% air. Microcultures derived from those cell suspensions (9, 3, or 1 cell/mL) producing cell growth in 20–60% of the seeded wells are screened for antibodies reactive with capture complex (positive). Five to ten positive cloned microcultures, originating from each positive primary culture, are cloned once again as described above. Approximately 5–10 clones per positive primary culture are selected for expansion of their cell numbers. Samples of these clones are cyropreserved while other samples are cultured in 75 cm sup 2 T flasks for antibody production. These MAbs are purified by affinity chromatography on a recombinant Protein G column and their specificity for BP-6-N7Gua is determined with a competitive ELISA.

Primary hybridoma cultures and both cloned and subcloned cultures are screened with a two-site labelled-antibody ELISA for selective binding with capture complex (BSA-MCC-BP-6-N7Gua) versus BSA-MCC-Gua and BSA-MCC-Methyl-N7Gua. Selected wells of 96well polystyrene ELISA plates are coated with capture complex, BSA-MCC-Gua or BSA-MCC-Methyl-N7Gua by addition of 100 µL of carbonate buffer (pH 9.6) containing 200 ng of conjugate and incubation overnight at 4 degrees C. The plates are washed 5 times with TBST buffer [0.05M Tris, 0.20M NaCl, 0.05% (v/v) Tween 20, pH 7.5], then blocked by addition of 200 µL blocking buffer [TBST with 1% (w/v) BSA] and incubation for 2.5 hours at 37 degrees C. The blocked plates are washed 5 times, then 100 µL of hybridoma culture medium diluted ⅒ with TBS buffer (0.05M Tris and 0.20M NaCl, pH 7.5) is added in duplicate to the appropriate wells. The plates are incubated for 30 minutes at 37 degrees C., then washed 5 times with TBST. One-hundred µL of horse radish peroxidase (HRP)-conjugated goat anti-mouse IgG antiserum diluted in TBS is added to the appropriate wells, then the plates are incubated for 30 minutes at 37 degrees C. The plates are washed 5 times with TBST, then 100 µL of the HRP substrate o-phenylenedaimine dihydrochloride [in citrate buffer (pH 4.5) containing 4 µL 30% hydrogen peroxide per 10 mL) is added to the wells. The plates are incubated in the dark for 30 minutes at room temperature, with constant agitation, then read with an ELISA reader set at 450 nm. Hybridoma culture media that produce a strong positive color reaction with capture complex and a weak or no color reaction with BSA-MCC-Gua or BSA-MCC-Methyl-N7Gua contain MAbs selective for capture complex and will be tested in the Competitive ELISA for specific binding with BP-6-N7Gua. Competitive Enzyme-linked Immunoabsorbent Assay (ELISA) For Determining MAB Specificity for 7-(Benzo [A]Pyren-6yl)Gua-Nine and for Quantifying 7-(Benzo[A] Pyren-6-yl)Guanine The following demonstrates a competitive ELISA that is used for both determining the specificity of capture complex selective MAbs for 7(Benzo[a]pyren-6-yl)Guanine and quantifying PAH-DNA adduct in biological fluids.

EXAMPLE 14

Competitive ELISA for 7-(Benzo[a]pyren-6-yl) Guanine

Screened MAbs selective for capture complex are tested for specific binding with BP-6-N7Gua in a competitive ELISA. Selected wells of 96-well polystyrene ELISA plates are coated with capture complex by addition of 100 µL of carbonate buffer (pH 9.6) containing 5–10 ng of conjugate and incubation overnight at 4 degrees C. The plates are washed 5 times with TBST buffer [0.05M Tris, 0.20M NaCl, 0.05% (v/v) Tween 20, pH 7.5], then blocked by addition of 200 µL blocking buffer [TBST w/ 1% (w/v) BSA] and incubation for 2.5 hours at 37 degrees C.

While the blocking reaction is progressing, NAb (selective for BP-6-N7Gua) and BP-6-N7Gua or benzo[a] pyrene (BP) or methylguanine (Me-N7Gua) or other structures related to BP-6-N7Gua are combined in separate Eppendorf tubes (1.5 mL polypropylene tubes). MAb is diluted 1:500 to 1:5000 in TBS buffer (0.05M Tris, 0.20M NaCl, pH 7.5) containing 10% (v/v) ethylene glycol as a protein stabilizer, then 500 uL is dispensed to each Eppendorf tube seated in a thermal mixing block set at 45 degrees C. These samples are heated for 10 minutes with vortexing. BP-6-N7Gua or BP or Me-N7Gua or other structures related to BP-6-N7Gua are diluted in methanol (MtOH), then added with vortexing in 10 uL volumes to duplicate samples of heated MAb solution. MtOH, alone, is added as a control to selected Eppendorfs. The reaction mixtures are heated with vortexing for an additional 20 minutes, then the reaction mixtures are cooled by addition of 100 uL of TBS buffer with 10% ethylene glycol. The reaction mixtures are incubated an additional 45 minutes at 37 degrees C.

At this point, blocking of the ELISA wells is complete and the reaction mixtures are added to the washed plates. The blocked plates are washed 5 times with TBST, then 100 uL of reaction mixture containing MAb and BP-6-N7Gua or BP or Me-N7Gua or other structure related to BP-6-N7Gua or MtOH, alone, is added to triplicate wells of-the coated and blocked ELISA plates. The plates are incubated at 37 degrees C. for 30 minutes, then washed 5 times with TBST. Secondary antibody consisting of goat anti-mouse IgG coupled with biotin is added to the wells and the plates are incubated at 37 degrees C. for 30 min. The plates are washed 5 times with TBST, then alkaline phosphatase coupled with streptavidin is added to the wells and the plates are washed 5 times with TBS. NADPH is added as substrate to the wells and the plates are incubated at 25 degrees C. for 20 minutes. During this period, NADPH is converted to NADH which acts as a cofactor in the next stage of signal generation. An amplifier mixture consisting of ethanol and the enzymes alcohol dehydrogenase and diaphorase is added directly to the wells. The amplifier system cycles NADH to NAD and back to NADH and for each NADH/NAD cycle generates a formazan chromophore. The plates are incubated an additional 20 minutes at 25 degrees C., then the reactions are stopped by addition of 0.3M sulfuric acid and read at 490 nm. The reaction between MAb and BP-6-N7Gua is seen as a reduction in signal production in comparison with the MtOH control. It is anticipated that for a MAb specific for BP-6-N7Gua the MAb signal will be reduced by very low concentrations of BP-6-N7Gua in comparison with those concentrations of BP or Me-N7Gua or other structures related to BP-N-7Gua required to produce the same signal reduction (generally 50% signal reduction is chosen as an endpoint). Those MAbs with high affinity for BP-6-N7Gua (low concentrations for 50% inhibition of the MAb signal) and low affinity for related structures e.g. guanine, methylguanine or benzo[a]pyrene (high concentrations for 50% inhibition of the MAb signal) will serve as tools for quantitation of urinary PAH-DNA adducts extracted with methanol.

Certain embodiments of the present invention have been described and exemplified hereinabove. However, the present invention is not limited to these embodiments, but is capable of variation and modification without departure from the scope of the appended claims.

What is claimed is:

1. A method for the chemical synthesis of adducts comprising a nucleoside component and another component selected from the group consisting of polycyclic aryl compounds and polycyclic heteroaryl compounds, said method comprising:

a) chemically oxidizing said polycyclic aryl or polycyclic heteroaryl compounds in an aprotic solvent to form a reactive intermediate;

b) contacting said reactive intermediate with said nucleoside under conditions causing formation of said adduct;

c) purifying said adduct; and d) recovering said purified adduct.

2. A method according to claim 1 wherein said nucleoside is selected from the group comprising deoxyadenosine, deoxyguanosine, deoxycytosine, or deoxythymidine.

3. A method according to claim 1 wherein said adduct is formed from a polycyclic hydrocarbon selected from the group comprising 7-12-dimethylbenz[a]anthracene, 7-methylbenz[a]anthracene, or benzo[a]pyrene.

4. A method according to claim 1 wherein said adduct is formed from a heteropolycyclic hydrocarbon 7-H-Dibenzo [c,g]carbazole.

5. A method according to claim 1 wherein said oxidizing agent is iodine.

6. A method according to claim 1 wherein said solvent is selected from the group consisting of dimethysulfoxide or dimethylformamide.

7. A method for the chemical synthesis of adducts comprising a nucleoside component and another component selected from the group consisting of polycyclic aryl compounds and polycyclic heteroaryl compounds , said method comprising:

a) mixing said polycyclic aromatic compounds with an aprotic solvent to form a reaction medium;

b) contacting said reaction medium containing said polycyclic compounds with an inorganic oxidizing agent, thereby forming a reactive intermediate;

c) reacting a nucleoside with said reactive intermediate to produce said adduct;

d) purifying said adduct using high performance liquid chromatography; and e) recovering said purified adduct.

8. A method for the chemical synthesis of adducts comprising a nucleoside component and another component selected from the group consisting of polycyclic aryl compounds and polycyclic heteroaryl compounds, said method comprising:

a) contacting said polycyclic aromatic compound with an aprotic solvent, thereby forming a reaction mixture;

b) oxidizing said polycyclic compounds present in said reaction mixture with iodine, thereby forming reactive intermediates;

c) contacting said reactive intermediates with a nucleoside under conditions causing nucleophilic groups present on said nucleoside to form adducts with said reactive intermediates;

d) reducing said iodine with a reducing agent;

e) removing said solvent from said reaction mixture, leaving a reaction residue;

f) extracting said polycyclic aromatic hydrocarbon-nucleoside adducts from said reaction residue with an extractant liquid;

g) isolating said polycyclic aromatic hydrocarbon-nucleoside adducts from said extractant liquid; and h) purifying said isolated polycyclic aromatic hydrocarbon-nucleoside adducts by HPLC.

9. A method for the chemical synthesis of adducts comprising a component selected from the group of bases consisting of adenine, thymidine, guanine, cytosine or uracil and another component selected from the group consisting of polycyclic aryl compounds and polycyclic heteroaryl compounds, said method comprising:

a) chemically oxidizing said polycyclic aryl or heteroaryl compound in the presence of a solvent with an inorganic oxidizing agent to form a reactive intermediate;

b) contacting said reactive intermediate with said base under conditions causing formation of said adduct;

c) purifying said adduct; and d) recovering said purified adduct.

10. A method according to claim 6 wherein said base is selected from the group comprising adenine, guanine, cytosine, thymidine or uracil.

11. A method according to claim 6 wherein said solvent is selected from the group consisting of dimethylsulfoxide or dimethylformamide.

12. A method according to claim 6 wherein said oxidizing agent is iodine.

13. A method according to claim 6 wherein said polycyclic hydrocarbon is selected from the group comprising 7-12-dimethylbenz[a]anthracene, 7-methylbenz[a]anthracene, or benzo[a]pyrene.

14. A method for the chemical synthesis of adducts comprising a base selected from the group consisting of adenine, thymidine, guanine, cytosine or uracil and another component selected from the group consisting of polycyclic aryl compounds and polycyclic heteroaryl compounds, said method comprising:

a) mixing said polycyclic aryl compound with an aprotic solvent to form a reaction medium;

b) contacting said reaction medium containing said polycyclic aryl compound with an inorganic oxidizing agent, thereby forming a reactive intermediate;

c) reacting said base with said reactive intermediate to produce said adduct;

d) purifying said adduct using high performance liquid chromatography; and e) recovering said purified adduct.

15. A method for the chemical synthesis of adducts comprising a base selected from the group consisting of adenine, thymidine, guanine, cytosine or uracil and another component selected from the group consisting of polycyclic aryl compounds and polycyclic heteroaryl compounds, said method comprising:

a) contacting said polycyclic aryl or polycyclic heteroaryl compound with a solvent, thereby forming a reaction mixture;

b) oxidizing said polycyclic aryl or polycyclic heteroaryl compound present in said reaction mixture with iodine, thereby forming reactive intermediates;

c) contacting said reactive intermediates with a base under conditions causing nucleophilic groups present on said base to form adducts with said reactive intermediates;

d) reducing said iodine with a reducing agent;

e) removing said solvent from said reaction mixture, leaving a reaction residue;

f) extracting said adducts from said reaction residue with an extractant liquid;

g) isolating said polycyclic or heteropolycylic aromatic hydrocarbon-base adducts from said extractant liquid; and h) purifying said polycyclic aromatic hydrocarbon-base adducts.

* * * * *